United States Patent
Cron et al.

(10) Patent No.: US 10,752,646 B2
(45) Date of Patent: Aug. 25, 2020

(54) METHOD OF MAKING PHOSPHONO-PHOSPHATE CONTAINING COMPOUNDS

(71) Applicant: The Procter & Gamble Company, Cincinnati, OH (US)

(72) Inventors: Scott Leroy Cron, Liberty Township, OH (US); Ryan M. West, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 16/215,704

(22) Filed: Dec. 11, 2018

(65) Prior Publication Data

US 2019/0177348 A1  Jun. 13, 2019

Related U.S. Application Data

(60) Provisional application No. 62/597,036, filed on Dec. 11, 2017.

(51) Int. Cl.
| | | |
|---|---|---|
| *C07F 9/40* | (2006.01) | |
| *C07F 9/38* | (2006.01) | |
| *C08F 30/02* | (2006.01) | |
| *A61Q 11/00* | (2006.01) | |
| *C08F 230/02* | (2006.01) | |
| *A61K 8/24* | (2006.01) | |
| *C07F 9/6571* | (2006.01) | |

(52) U.S. Cl.
CPC .............. *C07F 9/4015* (2013.01); *A61K 8/24* (2013.01); *A61Q 11/00* (2013.01); *C07F 9/3808* (2013.01); *C07F 9/409* (2013.01); *C07F 9/657181* (2013.01); *C08F 30/02* (2013.01); *C08F 230/02* (2013.01)

(58) Field of Classification Search
None
See application file for complete search history.

(56) References Cited

U.S. PATENT DOCUMENTS

| | | | |
|---|---|---|---|
| 2,946,725 | A | 7/1960 | Norris |
| 3,070,510 | A | 12/1962 | Cooley et al. |
| 3,678,154 | A | 7/1972 | Widder et al. |
| 3,959,458 | A | 5/1976 | Agricola et al. |
| 3,976,619 | A | 8/1976 | Morgan |
| 4,051,234 | A | 9/1977 | Gieske et al. |
| 4,416,877 | A | 11/1983 | Bentzen |
| 5,004,597 | A | 4/1991 | Majeti et al. |
| 5,281,410 | A | 1/1994 | Lukacovic et al. |
| 5,578,293 | A | 11/1996 | Prencipe et al. |
| 5,939,052 | A | 8/1999 | White, Jr. et al. |
| 6,173,049 | B1 | 1/2001 | Malik |
| 6,187,295 | B1 | 2/2001 | Glandorf |
| 6,190,644 | B1 | 2/2001 | McClanahan et al. |
| 6,350,436 | B1 | 2/2002 | Glandorf et al. |
| 6,713,049 | B1 | 3/2004 | White, Jr. |
| 7,399,756 | B2 | 7/2008 | Jomaa |
| 7,871,992 | B2 | 1/2011 | Jomaa |
| 8,017,596 | B2 | 9/2011 | Montero |
| 2005/0271602 | A1 | 12/2005 | Milanovich |
| 2006/0030546 | A1 | 2/2006 | Jomaa |
| 2006/0241087 | A1 | 10/2006 | Montero |
| 2008/0249067 | A1 | 10/2008 | Jomaa |
| 2010/0204184 | A1 | 8/2010 | Montero |
| 2011/0112054 | A1 | 5/2011 | Jomaa |
| 2016/0324741 | A1 | 11/2016 | Baig et al. |
| 2019/0175485 | A1 | 6/2019 | West |
| 2019/0177348 | A1 | 6/2019 | Cron |
| 2019/0177451 | A1 | 6/2019 | West |
| 2019/0177456 | A1 | 6/2019 | West |
| 2019/0177490 | A1 | 6/2019 | West |

FOREIGN PATENT DOCUMENTS

WO   WO2004017334   2/2004

OTHER PUBLICATIONS

U.S. Appl. No. 16/216,329, filed Dec. 11, 2018, Ryan M West et al.
U.S. Appl. No. 16/216,428, filed Dec. 11, 2018, Ryan M West et al.
U.S. Appl. No. 16/215,699, filed Dec. 11, 2018, Ryan M West et al.
U.S. Appl. No. 16/215,702, filed Dec. 11, 2018, Ryan M West et al.
Database WPI, Week 200425, Thomson Scientific, London GB, AN 2004-268983, XP002789049.
Ibrahim Zgani et al. "Synthesis of Prenyl Pyrophosphonates as New Potent Phosphorantigens Inducing Selective Activation of Human V[gamma] 9V[delta] 2 T Lymphocytes", Journal of Medicinal Chemistry, vol. 47, No. 18, Aug. 1, 2004, pp. 4600-4612, XP055569445.
International Search Report and Written Opinion dated Feb. 19, 2019, U.S. Appl. No. 16/215,704, 12 pgs.
International Search Report and Written Opinion dated Mar. 13, 2019, U.S. Appl. No. 16/215,702, 13 pgs.
International Search Report and Written Opinion dated Mar. 13, 2019, U.S. Appl. No. 16/216,039, 12 pgs.
International Search Report and Written Opinion dated Mar. 26, 2019, U.S. Appl. No. 16/215,699, 14 pgs.
Valentjin et al. "A novel approach towards the synthesis of pyrophosphate analogues of farnesyl pyrophosphate", Recl. Trav. Chim. pays-Bas, vol. 113, Dec. 12, 1944, pp. 563-566, XP002789048.
Anbar et al. "Organic Polymeric Polyphosphonates as Potential Preventive Agents of Dental Caries: In Vitro Experiments", J Dent Res, vol. 53, No. 4, pp. 867-878, 1974.

(Continued)

*Primary Examiner* — Samantha L Shterengarts
(74) *Attorney, Agent, or Firm* — James E Oehlenschlager; Jason J. Camp

(57) ABSTRACT

A method of making a phosphono-phosphate compound is disclosed. The method involves a first step of mixing a first component comprising a phosphonic acid, a phosphonate or mixtures thereof, with a second component comprising a source of phosphoric acid or phosphate. The mixture has a molar phosphorous ratio of the first component to the second component of from 1:1 to 1:10. The second step involves either physically or chemically dehydrating the mixture to produce a phosphono-phosphate compound.

26 Claims, No Drawings

(56) References Cited

OTHER PUBLICATIONS

Bingol et al., "Characterization of Oligo(vinyl phosphonate)s by High-Resolution Electrospray Ionization Mass Spectometry: Implications for the Mechanism of Polymerization", Macromolecules 2008, 41, pp. 1634-1639.
Brunet et al., "Engineering of Microcrystaline Solid-State Networks Using Cross-Linked y-Zirconium Phosphate/Hypophosphite with Nonrigid Polyethylenoxadiphosphonates. Easy Access to Porously Dynamic Solids with Polar/Nonpolar Pores", Chem. Mater. 2005, 17, pp. 1424-1433.
Frantz et al., "Synthesis and Solid-State NMR Studies of P-Vinylbenzylphosphonic Acid", Chemistry—A European Journal, vol. 9, Issue 3, pp. 770-775, 2003.
Kim et al., "Characterization of Poly(styrene-b-vinylbenzylphosphonic acid) Copolymer by Titration and Thermal Analysis", Macromolecular Research, vol. 15 No. 6, pp. 587-594, 2007.
Monge et al., "Polymerization of Phosphorus-Containing (Meth)acrylate Monomers", published May 7, 2014 http://pubs.rsc.org | doi:10.1039/9781782624523-00001, 18 pgs.
Schroeder et al., "The Reaction of Phosphorus Trichloride and Oxygen with Polymers", Journal of Polymer Science, vol. 47, Issue 149, pp. 417-433, 1960.
International Search Report with written opinion, dated Mar. 25, 2019, 14 pages, PCT/US2018/064885.
International Search Report with written opinion, dated Mar. 28, 2019, 11 pages, PCT/US2018/064883.

METHOD OF MAKING PHOSPHONO-PHOSPHATE CONTAINING COMPOUNDS

TECHNICAL FIELD OF THE INVENTION

The present invention relates to novel methods of making phosphono-phosphate containing compounds. More specifically, the present invention discloses preparing a mixture of first component comprising a phosphonic acid or a phosphonate with a second component comprising a source of phosphoric acid or phosphate and dehydrating the mixture.

BACKGROUND OF THE INVENTION

Chemical structures that interact with multivalent cations in solution and with surfaces containing multivalent cations are useful for manipulation of these systems. Polyphosphates and pyrophosphate, for example, have been used as builders in laundry and dish formulations to control calcium and in drilling muds to prevent precipitation. They have also been used in the oral care industry to help control tartar and reduce the thickness of the pellicle layer on teeth resulting in a slick tooth feel. Similarly, bisphosphonates, and hydroxy-bisphosphonates are active components in osteoporosis pharmaceuticals due to their strong interaction with calcium hydroxy apatite surfaces and are also used as crystal growth inhibitors in dishwashing liquids and boiler systems. Each of these examples suffer from an inherent limitation. Polyphosphates are prone to degradation over time in aqueous solutions at all pH's, ultimately leading to an increase in ortho phosphate in solution. Polyphosphate salts are also quite anionic in nature and are not soluble in non-polar organic systems. Polyphosphates are, however, generally safe for consumption and find use in different food products. Bisphosphonates and hydroxy-bisphosphonates are, conversely, stable in water for long periods of time, and can, depending upon the nature of the organic group attached to the bisphosphonate carbon, be made quite soluble in organic systems. Bisphosphonates, however, are bone active and hence cannot be used in foods or other systems where they might be accidently consumed due to their potent pharmacology. Polymers containing bisphosphonates of sufficient molecular weight to not pass through the intestinal wall would likely not be bone active, however any low molecular weight residual monomers or oligomers that could pass through the intestinal wall make the use of such polymers prohibitive in potential consumable contexts. In addition, since bisphosphonates do not break down readily, their activity can persist in the environment after use.

Therefore, a need still exists for a method of making a phosphate-like composition that interacts with multivalent cations in solution and with surfaces containing multivalent cations, that does not easily degrade, and that is safe for human consumption.

SUMMARY OF THE INVENTION

It has surprisingly been found that the phosphono-phosphate chemical group ameliorates the concerns of polyphosphates and bisphosphonates while finding utility in similar systems. In particular, compositions that contain a phosphono-phosphate group, monomers that contain a phosphono-phosphate group, and polymers that contain a phosphono-phosphate group, whether by incorporation of a monomer containing a phosphono-phosphate group, or by post polymerization modification to add a phosphono-phosphate group, can be used in numerous applications in which polyphosphates and bisphosphonate containing structures are used. Such applications generally include those in which binding interactions are involved with multivalent cations both in solution and on surfaces containing bivalent cations. Phosphono-phosphate containing structures can also be used in applications where polyphosphates and bisphosphonate use is limited. The phosphono-phosphate group is conditionally stable and will only release phosphate under acidic or catalyzed conditions. Hence the phosphono-phosphate group is more stable than polyphosphate, but not as stable as bisphosphonates. This enables formulation into systems where non-detrimental effects of consumption and water stability are a must. In addition, the organic group or polymer attached to the phosphono-phosphate group can cause the entire molecule to be soluble in organic solvents, or be used to add additional functionality to the entire molecule.

A method of making a phosphono-phosphate compound is disclosed. The method involves a first step of mixing a first component comprising a phosphonic acid, a phosphonate or mixtures thereof, with a second component comprising a source of phosphoric acid or phosphate. The mixture has a molar phosphorous ratio of the first component to the second component of from 1:1 to 1:10. The second step involves physically dehydrating the mixture to produce a phosphono-phosphate compound having the structure of Formula 1:

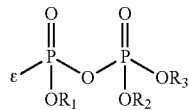

Formula 1 wherein:
ε is the site of attachment to a carbon atom;
R₁ is selected from the group consisting of —H, metal salt having Na, K, Ca, Mg, Mn, Zn, Fe, or Sn cation, amine cation salt, and a structure of Formula 2:

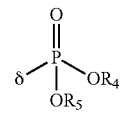

Formula 2 wherein:
δ is the site of attachment to Formula 1,
R₄ and R₅ are independently selected from the group consisting of —H, metal salt having Na, K, Ca, Mg, Mn, Zn, Fe, or Sn cation, and amine cation salt;
R₂ is selected from the group consisting of —H, metal salt having Na, K, Ca, Mg, Mn, Zn, Fe, or Sn cation, amine cation salt, and a structure of Formula 3:

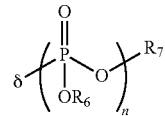

Formula 3 wherein:
  δ is the site of attachment to Formula 1,
  $R_6$, and $R_7$ are independently selected from the group consisting of —H, metal salt having Na, K, Ca, Mg, Mn, Zn, Fe, or Sn cation, and amine cation salt, and
  n is an integer from 1 to 2 and;
  $R_3$ is selected from the group consisting of —H, metal salt having Na, K, Ca, Mg, Mn, Zn, Fe, or Sn cation, and amine cation salt.

In a certain embodiment, the physical dehydration is accomplished by the evaporation of water. In another embodiment, the evaporation of water is performed at a temperature greater than 100° C. In one embodiment, the evaporation of water is performed at a pressure lower than atmospheric pressure. In another embodiment, the evaporation of water is performed with the aid of a sweep gas. In a certain embodiment, the evaporation of water is performed at a temperature greater than 100° C. and at a pressure lower than atmospheric. In another embodiment, the evaporation of water is performed at a temperature greater than 100° C., at a pressure lower than atmospheric, and with the aid of a sweep gas.

In a certain embodiment, the source of phosphoric acid or phosphate is selected from the group consisting of phosphoric acid, dihydrogen phosphate, monohydrogen phosphate, phosphate, pyrophosphoric acid, trihydrogen pyrophosphate, dihydrogen pyrophosphate, monohydrogen pyrophosphate, pyrophosphate, triphosphoric acid, tetrahydrogen triphosphate, trihydrogen triphosphate, dihydrogen triphosphate, monohydrogen triphosphate, triphosphate, mixtures of phosphorous pentoxide and water, and mixtures thereof. In another embodiment, the source of phosphoric acid or phosphate is phosphoric acid. In one embodiment, the source of phosphoric acid or phosphate is a mixture of phosphorous pentoxide and water. In another embodiment, the source of phosphoric acid or phosphate is phosphoric acid, phosphorous pentoxide, and water.

In an alternative embodiment, a method of making a phosphono-phosphate compound is disclosed. The method involves a first step of mixing a first component comprising a phosphonic acid, a phosphonate or mixtures thereof, with a second component comprising a source of phosphoric acid or phosphate. The mixture has a molar phosphorous ratio of the first component to the second component of from 1:1 to 1:10. The second step involves chemically dehydrating the mixture to produce a phosphono-phosphate compound with the structure of Formula 1:

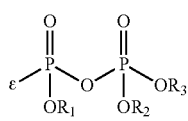

Formula 1 wherein:
  ε is the site of attachment to a carbon atom;
  $R_1$ is selected from the group consisting of —H, metal salt having Na, K, Ca, Mg, Mn, Zn, Fe, or Sn cation, amine cation salt, and a structure of Formula 2:

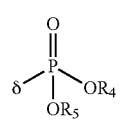

Formula 2 wherein:
  δ is the site of attachment to Formula 1,
  $R_4$ and $R_5$ are independently selected from the group consisting of —H, metal salt having Na, K, Ca, Mg, Mn, Zn, Fe, or Sn cation, and amine cation salt;
  $R_2$ is selected from the group consisting of —H, metal salt having Na, K, Ca, Mg, Mn, Zn, Fe, or Sn cation, amine cation salt, and a structure of Formula 3:

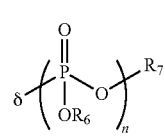

Formula 3 wherein:
  δ is the site of attachment to Formula 1,
  $R_6$, and $R_7$ are independently selected from the group consisting of —H, metal salt having Na, K, Ca, Mg, Mn, Zn, Fe, or Sn cation, and amine cation salt, and
  n is an integer from 1 to 2 and;
  $R_3$ is selected from the group consisting of —H, metal salt having Na, K, Ca, Mg, Mn, Zn, Fe, or Sn cation, and amine cation salt.

In a certain embodiment, the chemical dehydrating is accomplished by a chemical reaction with a chemical dehydration agent. In a another embodiment, the chemical dehydration agent is phosphorous pentoxide. In one embodiment, the source of phosphoric acid or phosphate is selected from the group consisting of phosphoric acid, dihydrogen phosphate, monohydrogen phosphate, phosphate, pyrophosphoric acid, trihydrogen pyrophosphate, dihydrogen pyrophosphate, monohydrogen pyrophosphate, pyrophosphate, triphosphoric acid, tetrahydrogen triphosphate, trihydrogen triphosphate, dihydrogen triphosphate, monohydrogen triphosphate, triphosphate, mixtures of phosphorous pentoxide and water, and mixtures thereof. In a certain embodiment, the source of phosphoric acid or phosphate is phosphoric acid. In another embodiment, the source of phosphoric acid or phosphate is a mixture of phosphorous pentoxide and water. In one embodiment, the source of phosphoric acid or phosphate is phosphoric acid, phosphorous pentoxide, and water. In a certain embodiment, the source of phosphoric acid or phosphate is a mixture of phosphorous pentoxide and water, and the chemical dehydrating is accomplished by use of a chemical dehydration agent wherein the chemical dehydration agent is phosphorous pentoxide.

In a certain embodiment, the method further involves the step of neutralizing the dehydrated mixture with a basic salt comprising Na, K, Ca, Mg, Mn, Zn, Fe, Sn, or amine cations. In another embodiment, the method further involves the step of: c) neutralizing the dehydrated mixture with an amine cation, and further reacting the resulting mixture with a basic salt comprising Na, K, Ca, Mg, Mn, Zn, Fe or Sn to form a metal phosphono-phosphate salt. In another embodiment, the method further involves the step of: d) precipitating the metal phosphono-phosphate salt from solution.

These and other features, aspects, and advantages of the present invention will become evident to those skilled in the art from reading of the present disclosure.

DETAILED DESCRIPTION OF THE INVENTION

While the specification concludes with claims particularly pointing and distinctly claiming the invention, it is believed the present invention will be better understood from the following description.

All percentages herein are by moles of the compositions unless otherwise indicated.

All ratios are molar ratios unless otherwise indicated.

All percentages, ratios, and levels of ingredients referred to herein are based on the actual amount of the ingredient by moles, and do not include solvents, fillers, or other materials with which the ingredient may be combined as commercially available products, unless otherwise indicated.

As used herein, "comprising" means that other steps and other ingredients which do not affect the end result can be added. This term encompasses the terms "consisting of" and "consisting essentially of".

All cited references are incorporated herein by reference in their entireties. Citation of any reference is not an admission regarding any determination as to its availability as prior art to the claimed invention.

Definitions

The terms "site" or "site of attachment" or "point of attachment" all mean an atom having an open valence within a chemical group or defined structural entity that is designated with a symbol such as a simple dash (-) or a lower case letter from the greek alphabet followed by a dash or a line (e.g. α-, β-, etc.) to indicate that the so-designated atom connects to another atom in a separate chemical group via a chemical bond. The symbol "〰" when drawn perpendicular across a bond

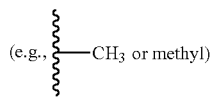

also indicates a point of attachment of a chemical group. It is noted that the point of attachment is typically only identified in this manner for larger chemical groups in order to unambiguously assist the reader in identifying the point of attachment to the atom from which the bond extends. A site or point of attachment on a first chemical group or defined structural entity connects to a site or point of attachment on a second chemical group or defined structural entity via either single, double, or triple covalent bonds in order to satisfy the normal valency of the atoms connected.

The term "radical" when used with a chemical group indicates any connected group of atoms, such as a methyl group, a carboxyl group, or a phosphono-phosphate group that is part of a larger molecule.

When used in the context of a chemical group: "hydrogen" means —H; "hydroxy" means —OH; "oxo" means =O; "carbonyl" means —C(=O)—; "carboxy" and "carboxylate" mean —C(=O)OH (also written as —COOH or —CO2H) or a deprotonated form thereof; "amino" means —NH2; "hydroxyamino" means —NHOH; "nitro" means —NO2; "imino" means =NH; "amine oxide" means N+O− where N has three covalent bonds to atoms other than O; "hydroxamic" or "hydroxamate" means —C(O)NHOH or a deprotonated form thereof; in a monovalent context "phosphate" means —OP(O)(OH)$_2$ or a deprotonated form thereof; in a divalent context "phosphate" means —OP(O)(OH)O— or a deprotonated form thereof; "phosphonate" means C—P(O)(OH)$_2$ or a deprotonated form thereof, where the C has a normal valence of four and three covalent bonds to atoms other than P; "phosphono-phosphate" means a phosphonate that is chemically bound through a shared oxygen atom to at least one phosphate such as but not limited to phosphono-monophosphate C—P(O)(OH)OP(O)(OH)$_2$, phosphono-diphosphate C—P(O)(OP(O)(OH)$_2$)OP(O)(OH)$_2$, phosphono-cyclodiphosphate

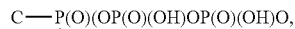

phosphono-pyrophosphate C—P(O)(OH)OP(O)(OH)OP(O)(OH)$_2$, and phosphono-polyphosphate C—P(O)(OH)(OP(O)(OH))$_n$OP(O)(OH)$_2$, where n is an integer between 1 and 100, or a deprotonated form thereof, where the C has a normal valence of four and three covalent bonds to atoms other than P; "phosphinate" means C—P(O)(OH)(C) or a deprotonated form thereof, where both C have a normal valence of four and three additional bonds to atoms other than P; "sulfate" means —OS(O)$_2$OH or deprotonated form thereof; "sulfonate" means CS(O)$_2$OH or a deprotonated form thereof where the C has a normal valence of four and three additional bonds to atoms other than S; "sulfinate" means CS(O)OH or a deprotonated form thereof, where the C has a normal valence of four and three additional bonds to atoms other than S; "mercapto" means —SH; "thio" means =S; "sulfonyl" means —S(O)$_2$—; and "sulfinyl" means —S(O)—.

For the chemical groups and classes below, the following parenthetical subscripts further define the chemical group/class as follows: "(Cn)" defines the exact number (n) of carbon atoms in the chemical group/class. "(C≤n)" defines the maximum number (n) of carbon atoms that can be in the chemical group/class, with the minimum number as small as possible for the chemical group in question, e.g., it is understood that the minimum number of carbon atoms in the chemical group "alkenyl$_{(C≤8)}$" or the chemical class "alkene$_{(C≤8)}$" is two. For example, "alkoxy$_{(C≤8)}$" designates those alkoxy groups having from 1 to 8 carbon atoms. (Cn-n') defines both the minimum (n) and maximum number (n') of carbon atoms in the chemical group. Similarly, alkyl$_{(C2-8)}$ designates those alkyl groups having from 2 to 8 carbon atoms, inclusive.

The term "cation" refers to an atom, molecule, or a chemical group with a net positive charge including single and multiply charged species. Cations can be individual atoms such as metals, non-limiting examples include Na$^+$ or Ca$^{+2}$, individual molecules, non-limiting examples include (CH$_3$)$_4$N$^+$, or a chemical group, non limiting examples include-N(CH$_3$)$_3$$^+$. The term "amine cation" refers to a particular molecular cation, of the form NR$_4$$^+$ where the four substituting R moieties can be independently selected from H and alkyl, non-limiting examples include NH$_4$$^+$ (ammonium), CH$_3$NH$_3$$^+$ (methylammonium), CH$_3$CH$_2$NH$_3$$^+$ (ethylammonium), (CH$_3$)$_2$NH$_2$$^+$ (dimethylammonium), (CH$_3$)$_3$NH$^+$ (trimethylammonium), and (CH$_3$)$_4$N$^+$ (tetramethylammonium).

The term "anion" refers to an atom, molecule, or chemical group with a net negative charge including single and multiply charged species. Anions can be individual atoms, for example but not limited to halides F$^-$, Cl$^-$, Br$^-$, individual molecules, non limiting examples include CO$_3$$^{-2}$, H$_2$PO$_4$$^-$, HPO$_4$$^{-2}$, PO$_4$$^{-3}$, HSO$_4$$^-$, SO$_4$$^{-2}$, or a chemical group, non limiting examples include sulfate, phosphate, sulfonate, phosphonate, phosphinate, sulfonate, mercapto, carboxylate, amine oxide, hydroxamate and hydroxyl amino. Deprotonated forms of previously defined chemical groups are considered anionic groups if the removal of the proton results in a net negative charge. In solutions, chemical groups are capable of losing a proton and become anionic as a function of pH according to the Henderson-Hasselbach equation (pH=pKa+$\log_{10}$([A$^-$]/[HA]; where [HA] is the molar concentration of an undissociated acid and [A$^-$] is the molar concentration of this acid's conjugate base). When the pH of the solution equals the pKa value of functional group, 50% of the functional group will be anionic, while the remaining 50% will have a proton. Typically, a functional group in solution can be considered anionic if the pH is at or above the pKa of the functional group.

The term "salt" or "salts" refers to the charge neutral combination of one or more anions and cations. For example, when R is denoted as a salt for the carboxylate group, —COOR, it is understood that the carboxylate (—COO—) is an anion with a negative charge −1, and that the R is a cation with a positive charge of +1 to form a charge neutral entity with one anion of charge −1, or R is a cation with a positive charge of +2 to form a charge neutral entity with two anions both of −1 charge.

The term "saturated" as used herein means the chemical compound or group so modified has no carbon-carbon double and no carbon-carbon triple bonds, except as noted below. In the case of substituted versions of saturated chemical groups, one or more carbon oxygen double bond or a carbon nitrogen double bond may be present. When such a bond is present, then carbon-carbon double bonds that may occur as part of keto-enol tautomerism or imine/enamine tautomerism are not precluded.

The term "aliphatic" when used without the "substituted" modifier signifies that the chemical compound/group so modified is an acyclic or cyclic, but non-aromatic hydrocarbon chemical compound or group. In aliphatic chemical compounds/groups, the carbon atoms can be joined together in straight chains, branched chains, or non-aromatic rings (alicyclic). Aliphatic chemical compounds/groups can be saturated, that is joined by single bonds (alkanes/alkyl), or unsaturated, with one or more double bonds (alkenes/alkenyl), or with one or more triple bonds (alkynes/alkynyl).

The term "alkyl" when used without the "substituted" modifier refers to a monovalent saturated aliphatic group with a carbon atom as the point of attachment, a linear or branched, cyclo, cyclic, or acyclic structure, and no atoms other than carbon and hydrogen. Thus, as used herein cycloalkyl is a subset of alkyl, with the carbon atom that forms the point of attachment also being a member of one or more non-aromatic ring structures wherein the cycloalkyl group consists of no atoms other than carbon and hydrogen. As used herein, the term does not preclude the presence of one or more alkyl groups (carbon number limitation permitting) attached to the ring or ring system. The groups —$CH_3$ (Me), —$CH_2CH_3$ (Et), —$CH_2CH_2CH_3$ (n-Pr or propyl), —$CH(CH_3)_2$ (i-Pr, 'Pr, or isopropyl), —$CH(CH_2)_2$ (cyclopropyl), —$CH_2CH_2CH_2CH_3$ (n-Bu), —$CH(CH_3)CH_2CH_3$ (sec-butyl), —$CH_2CH(CH_3)_2$ (isobutyl), —$C(CH_3)_3$ (tertbutyl, t-butyl, t-Bu, or tBu), —$CH_2C(CH_3)_3$ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —$CH_2$— (methylene), —$CH_2CH_2$—, —$CH_2C(CH_3)_2CH_2$—, and —$CH_2CH_2CH_2$— are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =$CH_2$, =$CH(CH_2CH_3)$, and =$C(CH_3)_2$. An "alkane" refers to the compound H—R, wherein R is alkyl as this term is defined above. When any of these terms is used with the "substituted" modifier one or more hydrogen atom has been independently replaced by —OH, —F, —Cl, —Br, —I, —$NH_2$, —$NO_2$, —$CO_2H$, —$CO_2CH_3$, —CN, —SH, —$OCH_3$, —$OCH_2CH_3$, —C(O)$CH_3$, —$NHCH_3$, —$NHCH_2CH_3$, —$N(CH_3)_2$, —C(O)$NH_2$, —OC(O)$CH_3$, —S(O)$_2NH_2$, —P(O)(OH)$_2$, —P(O)(OH)OP(O)(OH)$_2$, —OP(O)(OH)$_2$, —OP(O)(OH)OP(O)(OH)$_2$, —S(O)$_2$(OH), or —OS(O)$_2$(OH). The following groups are non-limiting examples of substituted alkyl groups: —$CH_2OH$, —$CH_2Cl$, —$CF_3$, —$CH_2CN$, —$CH_2C(O)OH$, —$CH_2C(O)OCH_3$, —$CH_2C(O)NH_2$, —$CH_2C(O)CH_3$, —$CH_2OCH_3$, —$CH_2OC(O)CH_3$, —$CH_2NH_2$, —$CH_2N(CH_3)_2$, —$CH_2CH_2Cl$, —$CH_2P(O)(OH)_2$, —$CH_2P(O)(OH)OP(O)(OH)_2$, —$CH_2S(O)_2(OH)$, and —$CH_2OS(O)_2(OH)$. The term "haloalkyl" is a subset of substituted alkyl, in which one or more hydrogen atoms has been substituted with a halo group and no other atoms aside from carbon, hydrogen and halogen are present. The group, —$CH_2Cl$ is a non-limiting example of a haloalkyl. The term "fluoroalkyl" is a subset of substituted alkyl, in which one or more hydrogen has been substituted with a fluoro group and no other atoms aside from carbon, hydrogen and fluorine are present. The groups, —$CH_2F$, —$CF_3$, and —$CH_2CF_3$ are non-limiting examples of fluoroalkyl groups.

That term "chemically dehydrating" means decreasing the concentration of water in one phase by reacting the water with a second chemical to produce products that do not contain free water. One nonlimiting example of chemically dehydrating a phase is the reaction of water with carboxylic acid anhydrides, such as acetic anhydride where the product is two carboxylic acids, in this case two acetic acids. A second nonlimiting example is reaction with phosphorous oxides where the ratio of oxygen to phosphorous is less than 4, such as pyrophosphoric acid with a ratio O:P of 7:2, or phosphorous anhydride ($P_2O_5$, Phosphorous pentoxide) with a ratio of O:P of 5:2. A third nonlimiting example is a dehydrating salt such as $MgSO_4$, which when reacted with water produces a hydrated form that does not contain free water. A fourth nonlimiting example is a reactive metal such as Na metal with an oxidation state of zero.

The term "phosphonoalkyl" is a subset of substituted alkyl, in which one or more of the hydrogen has been substituted with a phosphonate group and no other atoms aside from carbon, hydrogen, phosphorous, and oxygen are present. The groups, —$CH_2P(O)(OH)_2$, and —$CH_2CH_2P(O)(OH)_2$, and the corresponding deprotonated forms thereof, are non-limiting examples of a phosphonoalkyl.

The term "phosphono(phosphate)alkyl" is a subset of substituted alkyl, in which one or more of the hydrogen has been substituted with a phosphono-phosphate group and no other atoms aside from carbon, hydrogen, phosphorous, and oxygen are present. The groups, —$CH_2P(O)(OH)OP(O)(OH)_2$, and —$CH_2CH_2P(O)(OH)OP(O)(OH)_2$, and corresponding deprotonated forms thereof, are non-limiting examples of phosphono(phosphate)alkyl.

The term "physically dehydrating" means decreasing the concentration of water in one phase by removal to another phase. Examples of physically dehydrating a phase include evaporation (removal of water from a liquid phase to a gaseous phase), adsorption (removal of water from a liquid phase to the surface of a solid phase), extraction (removal of water from a liquid phase into a separate immiscible liquid phase), crystallization (removal of water from a liquid phase into a solid phase).

The term "sulfonoalkyl" is a subset of substituted alkyl, in which one or more of the hydrogen has been substituted with a sulfonate group and no other atoms aside from carbon, hydrogen, sulfur, and oxygen are present. The groups, —CH$_2$S(O)$_2$OH and —CH$_2$CH$_2$S(O)$_2$OH, and the corresponding deprotonated forms thereof, are non-limiting examples of a sulfonoalkyl.

The term "alkenyl" when used without the "substituted" modifier refers to an monovalent unsaturated aliphatic group with a carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —C(CH$_3$)=CH$_2$ (methyl-vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, >C=CH$_2$ (vinylidine), —CH=CH—, —CH=C(CH$_3$)CH$_2$—, and —CH=CHCH$_2$—, are non-limiting examples of alkenediyl groups. It is noted that while the alkenediyl group is aliphatic, once connected at both ends, this group is not precluded from forming part of an aromatic structure. The terms "alkene" or "olefin" are synonymous and refer to a compound having the formula H—R, wherein R is alkenyl as this term is defined above. A "terminal alkene" refers to an alkene having just one carbon-carbon double bond, wherein that bond forms a vinyl group at one end of the molecule. When any of these terms are used with the "substituted" modifier one or more hydrogen atom has been independently replaced by —OH, —F, —Cl, —Br, —I, —NH, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —CH=CHF, —CH=CHCl and —CH=CHBr, are non-limiting examples of substituted alkenyl groups.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH$_3$, and —CH$_2$C≡CCH$_3$, are non-limiting examples of alkynyl groups. An "alkyne" refers to the compound H—R, wherein R is alkynyl.

When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "aryl" when used without the "substituted" modifier refers to a monovalent unsaturated aromatic group with an aromatic carbon atom as the point of attachment, said carbon atom forming part of a one or more six membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (~Ph), methylphenyl, (dimethyl)phenyl, —C$_6$H$_4$CH$_2$CH$_3$ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

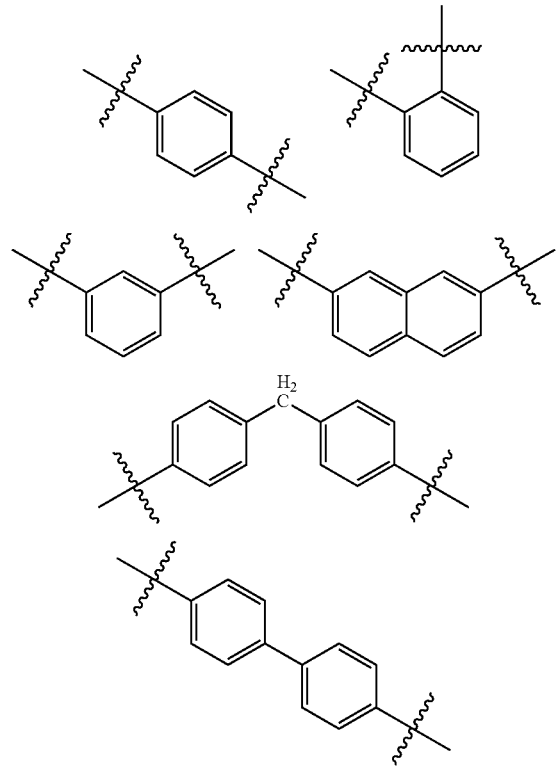

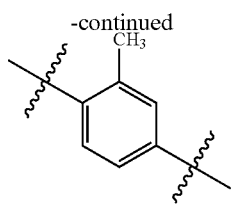

An "arene" refers to the compound H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "acyl" when used without the "substituted" modifier refers to the group —C(O)R, in which R is a hydrogen, alkyl, aryl, aralkyl or heteroaryl, as those terms are defined above. The groups, —CHO (formyl), —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. When any of these terms are used with the "substituted" modifier one or more hydrogen atom (including a hydrogen atom directly attached the carbonyl or thiocarbonyl group, if any) has been independently replaced by —OH, —F, —Cl, —Br, —I, —NH2, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —C(O)CH$_2$CF$_3$, —CO$_2$H (carboxyl), —CO$_2$CH$_3$(methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH$_3$ (methoxy), —OCH$_2$CH$_3$ (ethoxy), —OCH$_2$CH$_2$CH$_3$, —OCH(CH$_3$)$_2$ (isopropoxy), —O(CH$_3$)$_3$ (tert-butoxy), —OCH(CH$_2$)$_2$, —O-cyclopentyl, and —O-cyclohexyl. The terms "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is alkenyl, alkynyl, aryl, aralkyl, heteroaryl, heterocycloalkyl, and acyl, respectively. The term "alkoxydiyl" refers to the divalent group —O-alkanediyl-, —O-alkanediyl-O—, or -alkanediyl-O-alkanediyl-. The term "alkanediyl-alkoxy" refers to -alkanediyl-O-alkyl. A non-limiting example of alkanedyl-alkoxy is —CH$_2$—CH$_2$—O—CH$_2$—CH$_3$. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "alkenylamino", "alkynylamino", "arylamino", "aralkylamino", "heteroarylamino", "heterocycloalkylamino" and "alkylsulfonylamino" when used without the "substituted" modifier, refers to groups, defined as —NHR, in which R is alkoxy, alkenyl, alkynyl, aryl, aralkyl, heteroaryl, heterocycloalkyl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. The term "alkylaminodiyl" refers to the divalent group —NH-alkanediyl-, —NH-alkanediyl-NH—, or -alkanediyl-NH-alkanediyl-. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups —NHC(O)OCH$_3$ and —NHC(O)NHCH$_3$ are non-limiting examples of substituted amido groups.

The terms "alkylsulfonyl" and "alkylsulfinyl" when used without the "substituted" modifier refers to the groups —S(O)$_2$R and —S(O)R, respectively, in which R is an alkyl, as that term is defined above. The terms "alkenylsulfonyl", "alkynylsulfonyl", "arylsulfonyl", "aralkylsulfonyl", "heteroarylsulfonyl", and "heterocycloalkylsulfonyl" are defined in an analogous manner. When any of these terms is used with the "substituted" modifier one or more hydrogen atom has been independently replaced by —OH, —F, —Cl, —Br, —I, —NH2, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "alkylphosphate" when used without the "substituted" modifier refers to the group —OP(O)(OH)(OR) or a deprotonated form thereof, in which R is an alkyl, as that term is defined above. Nonlimiting examples of alkylphosphate groups include: —OP(O)(OH)(OMe) and —OP(O)(OH)(OEt). The term "dialkylphosphate" when used without the "substituted" modifier refers to the group —OP(O)(OR)(OR'), in which R and R' can be the same or different alkyl groups, or R and R' can be taken together to represent an alkanediyl. Non-limiting examples of dialkylphosphate groups include: —OP(O)(OMe)$_2$, —OP(O)(OEt)(OMe) and —OP(O)(OEt)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

Linking group means either a covalent bond between two other defined groups, or a series of covalently bound atoms that connect two other defined groups wherein the series of covalently bound atoms have no open valences other than the sites of attachment to the two other defined groups. Non-limiting examples of a linking group include a covalent bond, alkanediyl, alkenediyl, arenediyl, alkoxydiyl, and alkylaminodiyl.

As used herein, a "chiral auxiliary" refers to a removable chiral group that is capable of influencing the stereoselectivity of a reaction. Persons of skill in the art are familiar with such compounds, and many are commercially available.

Phosphorous pentoxide means the chemical with CAS Registry Number 1314-56-3, and a chemical composition of P$_2$O$_5$. Phosphorous pentoxide is also known as diphosphorous pentaoxide, diphosphorous pentoxide, phosphoric acid anhydride, phosphoric anhydride, phosphoric oxide, phosphoric pentoxide, phosphoric pentaoxide, phosphorous oxide, phosphorus pentaxode, and phosphorous pentoxide.

Other abbreviations used herein are as follows: DMSO, dimethyl sulfoxide; DMF, dimethylformamide; MeCN, acetonitrile; MeOH, methanol; EtOH, ethanol; EtOAc, ethyl acetate; tBuOH, tert-butanol; iPrOH, isopropanol; cHexOH, cyclohexanol; Ac$_2$O, acetic anhydride; AcOOH, peracetic acid; HCO$_2$Et, ethyl formate; THF, tetrahydrofuran; MTBE, methyl tert-butyl ether; DME, dimethoxyethane; NBS, N-bromosuccinimide; CDI, carbonyldiimidazole; DIEA, diisopropylethylamine; TEA, triethylamine; DMAP, dimethylaminopyridine; NaOH, sodium hydroxide; AAPH, 2,2'-azobis(2-methylpropionamidine) dihydrochloride; CTA, 1-Octanethiol; APS, ammonium persulfate; TMP, trimethyl phosphate; VPA, vinyl phosphonic acid; VPP, vinyl phosphono-monophosphate; VPPP, vinyl phosphono-pyro-phosphate MVPP, methyl-vinyl phosphono-monophosphate; SVS, sodium vinyl sulfonate; AMPS, sodium 2-acrylamido-2-methyl propane sulfonic acid; SPA, 3-sulfopropyl acrylate potassium salt; 22A2MPA2HCl, 2,2'-azobis (2-methylpropionamidine) dihydrochloride; VBPP, (4-vinylbenzyl)monophosphono-phosphate; VSME, vinyl sulfonate methyl ester; NaOMe, sodium methoxide; NaCl, sodium chloride; DMVP, dimethyl vinyl phosphonate A "monomer molecule" is defined by the International Union of Pure and Applied Chemistry (IUPAC) as "A molecule which can undergo polymerization thereby contributing constitutional units to the essential structure of a macromolecule." A polymer is a macromolecule.

A "polymer backbone" or "main chain" is defined by IUPAC as "That linear chain to which all other chains, long or short, or both may be regarded as being pendant" with the note that "Where two or more chains could equally be considered to be the main chain, that one is selected which leads the simplest representation of the molecule." Backbones can be of different chemical compositions depending upon the starting materials from which they are made. Common backbones from chemically and biologically synthesized polymers include alkanes, typically from vinyl or methyl vinyl polymerizations or cationic and anionic polymerizations, poly esters, from condensation polymerizations, poly amides, such as poly peptides from polymerizations involving amidation reactions, and poly ethoxylates from epoxide ring opening.

A "pendant group" or "side group" is defined by IUPAC as "An offshoot, neither oligomeric nor polymeric from a chain." A side group as such does not include a linear repeated unit.

A "polymer side chain" or "pendant chain" is defined by IUPAC as "An oligomeric or polymeric offshoot from a macromolecular chain" with the additional notes that "An oligomeric branch may be termed a short chain branch" and "A polymeric branch may be termed a long chain branch".

"Post-polymerization modification" is defined as any reaction or treatment of a polymer that takes place following polymerization. Post-polymerization modifications include reactions to chemical groups within or attached to the polymer backbone, pendant group, or polymer side chains.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The above definitions supersede any conflicting definition in any reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

Methods of Making the Polymers

In one embodiment, the method of the present invention involves a first step of mixing a first component comprising a phosphonic acid, a phosphonate or mixtures thereof, with a second component comprising a source of phosphoric acid or phosphate. The mixture has a molar phosphorous ratio of the first component to the second component of from 1:1 to 1:10. The second step involves physically dehydrating the mixture to produce a phosphono-phosphate compound having the structure of Formula 1:

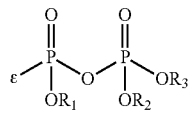

Formula 1 wherein:

ε is the site of attachment to a carbon atom;

R$_1$ is selected from the group consisting of —H, metal salt having Na, K, Ca, Mg, Mn, Zn, Fe, or Sn cation, amine cation salt, and a structure of Formula 2:

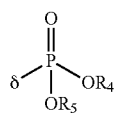

Formula 2 wherein:
δ is the site of attachment to Formula 1,
$R_4$ and $R_5$ are independently selected from the group consisting of —H, metal salt having Na, K, Ca, Mg, Mn, Zn, Fe, or Sn cation, and amine cation salt;
$R_2$ is selected from the group consisting of —H, metal salt having Na, K, Ca, Mg, Mn, Zn, Fe, or Sn cation, amine cation salt, and a structure of Formula 3:

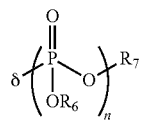

Formula 3 wherein:
δ is the site of attachment to Formula 1,
$R_6$, and $R_7$ are independently selected from the group consisting of —H, metal salt having Na, K, Ca, Mg, Mn, Zn, Fe, or Sn cation, and amine cation salt, and n is an integer from 1 to 2 and;
$R_3$ is selected from the group consisting of —H, metal salt having Na, K, Ca, Mg, Mn, Zn, Fe, or Sn cation, and amine cation salt.

In one embodiment, $R_1$, $R_2$, and $R_3$ are independently selected from the group consisting of H, Na salt, and K salt. In one embodiment, $R_1$, $R_2$, and $R_3$ are H.

In another embodiment, $R_1$ has the structure of Formula 2. In a further embodiment $R_1$ has the structure of Formula 2 and $R_4$ and $R_5$ are independently selected from H, Na salt, and K salt. In a further embodiment $R_2$ has the structure of Formula 2 and $R_4$ and $R_5$ are independently selected from H, Na salt, K salt, Zn salt, Ca salt, Sn salt, and amine cation salt.

In another embodiment, $R_2$ has the structure of Formula 3. In another embodiment $R_2$ has the structure of Formula 3 and n is 1. In another embodiment, $R_2$ has the structure of Formula 3 and $R_6$ and $R_7$ are independently selected from H, Na salt, and K salt. In another embodiment, $R_3$ has the structure of Formula 3 and $R_6$ and $R_7$ are independently selected from H, Na salt, K salt, Zn salt, Ca salt, Sn salt, and amine cation salt. In another embodiment, $R_2$ has the structure of Formula 3, $R_6$ and $R_7$ are independently selected from H, Na salt, K salt, Zn salt, Ca salt, Sn salt, and amine cation salt and n is 1.

In a certain embodiment, the physical dehydration is accomplished by the evaporation of water. In another embodiment, the evaporation of water is performed at a temperature greater than 100° C. In one embodiment, the evaporation of water is performed at a pressure lower than atmospheric pressure. In another embodiment, the evaporation of water is performed with the aid of a sweep gas. In a certain embodiment, the evaporation of water is performed at a temperature greater than 100° C. and at a pressure lower than atmospheric. In another embodiment, the evaporation of water is performed at a temperature greater than 100° C., at a pressure lower than atmospheric, and with the aid of a sweep gas.

In a certain embodiment, the source of phosphoric acid or phosphate is selected from the group consisting of phosphoric acid, dihydrogen phosphate, monohydrogen phosphate, phosphate, pyrophosphoric acid, trihydrogen pyrophosphate, dihydrogen pyrophosphate, monohydrogen pyrophosphate, pyrophosphate, triphosphoric acid, tetrahydrogen triphosphate, trihydrogen triphosphate, dihydrogen triphosphate, monohydrogen triphosphate, triphosphate, mixtures of phosphorous pentoxide and water, and mixtures thereof. In another embodiment, the source of phosphoric acid or phosphate is phosphoric acid. In one embodiment, the source of phosphoric acid or phosphate is a mixture of phosphorous pentoxide and water. In another embodiment, the source of phosphoric acid or phosphate is phosphoric acid, phosphorous pentoxide, and water.

In a certain embodiment, the method further involves the step of neutralizing the dehydrated mixture with a basic salt comprising Na, K, Ca, Mg, Mn, Zn, Fe, Sn, or amine cations. In another embodiment, the method further involves the step of: c) neutralizing the dehydrated mixture with an amine cation, and further reacting the resulting mixture with a basic salt comprising Na, K, Ca, Mg, Mn, Zn, Fe or Sn to form a metal phosphono-phosphate salt. In another embodiment, the method further involves the step of: d) precipitating the metal phosphono-phosphate salt from solution.

In a certain embodiment the said ratio of first component to the second component is from 1:1 to 1:8. In a another embodiment the said ratio of first component to the second component is from 1:1 to 1:6. In a another embodiment the said ratio of first component to the second component is from 1:3 to 1:6.

In an alternative embodiment, a method of making a phosphono-phosphate compound is disclosed. The method involves a first step of mixing a first component comprising a phosphonic acid, a phosphonate or mixtures thereof, with a second component comprising a source of phosphoric acid or phosphate. The mixture has a molar phosphorous ratio of the first component to the second component of from 1:1 to 1:10. The second step involves chemically dehydrating the mixture to produce a phosphono-phosphate compound with the structure of Formula 1:

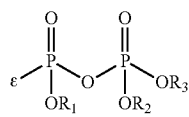

Formula 1 wherein:
ε is the site of attachment to a carbon atom;
$R_1$ is selected from the group consisting of —H, metal salt having Na, K, Ca, Mg, Mn, Zn, Fe, or Sn cation, amine cation salt, and a structure of Formula 2:

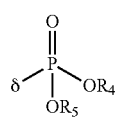

Formula 2 wherein:
δ is the site of attachment to Formula 1,
$R_4$ and $R_5$ are independently selected from the group consisting of —H, metal salt having Na, K, Ca, Mg, Mn, Zn, Fe, or Sn cation, and amine cation salt;
$R_2$ is selected from the group consisting of —H, metal salt having Na, K, Ca, Mg, Mn, Zn, Fe, or Sn cation, amine cation salt, and a structure of Formula 3:

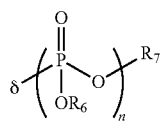

Formula 3 wherein:
δ is the site of attachment to Formula 1,
$R_6$, and $R_7$ are independently selected from the group consisting of —H, metal salt having Na, K, Ca, Mg, Mn, Zn, Fe, or Sn cation, and amine cation salt, and n is an integer from 1 to 2 and;
$R_3$ is selected from the group consisting of —H, metal salt having Na, K, Ca, Mg, Mn, Zn, Fe, or Sn cation, and amine cation salt.

In one embodiment, $R_1$, $R_2$, and $R_3$ are independently selected from the group consisting of H, Na salt, and K salt. In one embodiment, $R_1$, $R_2$, and $R_3$ are H.

In another embodiment, $R_1$ has the structure of Formula 2. In a further embodiment $R_1$ has the structure of Formula 2 and $R_4$ and $R_5$ are independently selected from H, Na salt, and K salt. In a further embodiment $R_2$ has the structure of Formula 2 and $R_4$ and $R_5$ are independently selected from H, Na salt, K salt, Zn salt, Ca salt, Sn salt, and amine cation salt.

In another embodiment, $R_2$ has the structure of Formula 3. In another embodiment, $R_2$ has the structure of Formula 3 and n is 1. In another embodiment, $R_2$ has the structure of Formula 3 and $R_6$ and $R_7$ are independently selected from H, Na salt, and K salt. In another embodiment, $R_3$ has the structure of Formula 3 and $R_6$ and $R_7$ are independently selected from H, Na salt, K salt, Zn salt, Ca salt, Sn salt, and amine cation salt. In another embodiment, $R_2$ has the structure of Formula 3, $R_6$ and $R_7$ are independently selected from H, Na salt, K salt, Zn salt, Ca salt, Sn salt, and amine cation salt and n is 1.

In a certain embodiment, the chemical dehydrating is accomplished by a chemical reaction with a chemical dehydration agent. In another embodiment, the chemical dehydration agent is phosphorous pentoxide. In one embodiment, the source of phosphoric acid or phosphate is selected from the group consisting of phosphoric acid, dihydrogen phosphate, monohydrogen phosphate, phosphate, pyrophosphoric acid, trihydrogen pyrophosphate, dihydrogen pyrophosphate, monohydrogen pyrophosphate, pyrophosphate, triphosphoric acid, tetrahydrogen triphosphate, trihydrogen triphosphate, dihydrogen triphosphate, monohydrogen triphosphate, triphosphate, mixtures of phosphorous pentoxide and water, and mixtures thereof. In a certain embodiment, the source of phosphoric acid or phosphate is phosphoric acid. In another embodiment, the source of phosphoric acid or phosphate is a mixture of phosphorous pentoxide and water. In one embodiment, the source of phosphoric acid or phosphate is phosphoric acid, phosphorous pentoxide, and water. In a certain embodiment, the source of phosphoric acid or phosphate is a mixture of phosphorous pentoxide and water, and the chemical dehydrating is accomplished by use of a chemical dehydration agent wherein the chemical dehydration agent is phosphorous pentoxide.

In a certain embodiment, the method further involves the step of neutralizing the dehydrated mixture with a basic salt comprising Na, K, Ca, Mg, Mn, Zn, Fe, Sn, or amine cations. In another embodiment, the method further involves the step of: c) neutralizing the dehydrated mixture with an amine cation, and further reacting the resulting mixture with a basic salt comprising Na, K, Ca, Mg, Mn, Zn, Fe or Sn to form a metal phosphono-phosphate salt. In another embodiment, the method further involves the step of: d) precipitating the metal phosphono-phosphate salt from solution.

In a certain embodiment the said ratio of first component to the second component is from 1:1 to 1:8. In a another embodiment the said ratio of first component to the second component is from 1:1 to 1:6. In a another embodiment the said ratio of first component to the second component is from 1:3 to 1:6.

In all previous embodiments whether using a physical dehydration or a chemical dehydration to produce a phosphono-phosphate compound, c is the site of attachment to a carbon atom. The additional atoms attached to this specific carbon atom can be quite varied. In a further embodiment, E is the site of attachment to a carbon atom in a small molecule. In a further embodiment, c is the site of attachment to a carbon atom in a polymer. In a further embodiment, c is the site of attachment to a carbon atom in a polymer backbone. In a further embodiment, c is the site of attachment to a carbon atom in a polymer side chain. In a further embodiment, c is the site of attachment to a carbon atom in a polymer side group.

In one embodiment when ε is the site of attachment to a carbon atom in a small molecule, the molecule has the structure of Formula 4:

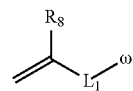

Formula 4 wherein:
ω is the site of attachment to the phosphono-phosphate group of Formula 1;
$R_8$ is selected from the group consisting of —H and —$CH_3$;
$L_1$ is selected from the group consisting of a chemical bond, arenediyl, and a structure of Formula 5:

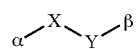

Formula 5 wherein:
α is the site of attachment to the alkenyl radical;
β is the site of attachment to the phosphono-phosphate group of Formula 1;
X is selected from the group consisting of the structures in Formulas 6-12;

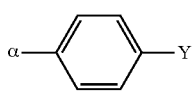

Formula 6

-continued

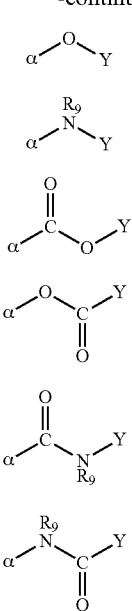

Formula 7

Formula 8

Formula 9

Formula 10

Formula 11

Formula 12 wherein:
$R_9$ is selected from the group consisting of —H, alkyl $_{(C1-8)}$, phosphonoalkyl, and phosphono(phosphate) alkyl; and
Y is selected from the group consisting of alkanediyl, alkoxydiyl, alkylaminodiyl and alkenediyl.

In one embodiment, when ε is the site of attachment to a carbon atom in a small molecule with the structure of Formula 4, $R_8$ is H. In another embodiment, when ε is the site of attachment to a carbon atom in a small molecule with the structure of Formula 4, $R_8$ is $CH_3$. In yet another embodiment, when ε is the site of attachment to a carbon atom in a small molecule with the structure of Formula 4, $L_1$ is a covalent bond. In one embodiment, when ε is the site of attachment to a carbon atom in a small molecule with the structure of Formula 4, $R_8$ is H, and $L_1$ is a covalent bond. In one embodiment, when ε is the site of attachment to a carbon atom in a small molecule with the structure of Formula 4, $R_8$ is $CH_3$, and $L_1$ is a covalent bond.

In another embodiment, when ε is the site of attachment to a carbon atom in a small molecule with the structure of Formula 4, $L_1$ has the structure of Formula 5 and X has the structure of Formula 6. In yet another embodiment, when ε is the site of attachment to a carbon atom in a small molecule with the structure of Formula 4, $L_1$ has the structure of Formula 5 and X has the structure of Formula 9. In one embodiment, when ε is the site of attachment to a carbon atom in a small molecule with the structure of Formula 4, $L_1$ has the structure of Formula 5 and X has the structure of Formula 11. In another embodiment when ε is the site of attachment to a carbon atom in a small molecule with the structure of Formula 4, $L_1$ has the structure of Formula 5 and X has the structure of Formula 7. In another embodiment when ε is the site of attachment to a carbon atom in a small molecule with the structure of Formula 4, $L_1$ has the structure of Formula 5, X has the structure of Formula 6 and Y is alkanediyl. In another embodiment when ε is the site of attachment to a carbon atom in a small molecule with the structure of Formula 4, $L_1$ has the structure of Formula 5, X has the structure of Formula 9 and Y is alkanediyl. In another embodiment when ε is the site of attachment to a carbon atom in a small molecule with the structure of Formula 4, $L_1$ has the structure of Formula 5, X has the structure of Formula 11 and Y is alkanediyl. In another embodiment when ε is the site of attachment to a carbon atom in a small molecule with the structure of Formula 4, $L_1$ has the structure of Formula 5, X has the structure of Formula 7 and Y selected from the group consisting of alkanediyl and alkoxydiyl.

In one embodiment when ε is the site of attachment to a carbon atom in a polymer, the polymer has the structure of Formula 13;

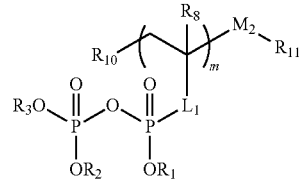

Formula 13

$R_1$ is selected from the group consisting of —H, Na, K, Ca, Mg, Mn, Zn, Fe, Sn, amine cations, and a structure of Formula 2:

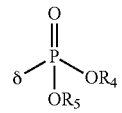

Formula 2 wherein:
δ is the site of attachment to Formula 13,
$R_4$ and $R_5$ are independently selected from the group consisting of —H, Na, K, Ca, Mg, Mn, Zn, Fe, Sn, and amine cations;
$R_2$ is selected from the group consisting of —H, Na, K, Ca, Mg, Mn, Zn, Fe, Sn, amine cations, and a structure of Formula 3:

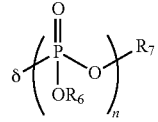

Formula 3 wherein:
δ is the site of attachment to Formula 13,
$R_6$, and $R_7$ are independently selected from the group consisting of —H, Na, K, Ca, Mg, Mn, Zn, Fe, Sn, and amine cations, and
n is an integer from 1 to 2 and;
$R_3$ is selected from the group consisting of —H, Na, K, Ca, Mg, Mn, Zn, Fe, Sn, and amine cations, and
$R_8$ is selected from the group consisting of —H and —$CH_3$;
$L_1$ is selected from the group consisting of a chemical bond, arenediyl, and a structure of Formula 5:

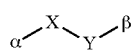

Formula 5 wherein:
α is the site of attachment to the polymer backbone;
β is the site of attachment to the phosphono-phosphate of Formula 13;
X is selected from the group consisting of the structures in Formulas 6-12;

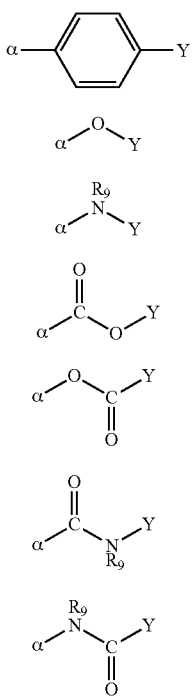

Formula 6
Formula 7
Formula 8
Formula 9
Formula 10
Formula 11
Formula 12 wherein:
$R_9$ is selected from the group consisting of —H, alkyl$_{(C1-8)}$, phosphonoalkyl, and phosphono(phosphate)alkyl; and
Y is selected from the group consisting of alkanediyl, alkoxydiyl, alkylaminodiyl and alkenediyl,
$R_{10}$ is a chemical group resulting from polymer initiation;
$R_{11}$ is a chemical group resulting chain termination;
$M_2$ is selected from the group consisting of a chemical bond and the post polymerization residue of one or more co-monomers; and
m is an integer from 2 to 450.

In one embodiment when ε is the site of attachment to a carbon atom in a polymer, $R_1$, $R_2$, and $R_3$ are independently selected from the group consisting of H, Na salt, and K salt. In one embodiment when ε is the site of attachment to a carbon atom in a polymer, $R_1$, $R_2$, and $R_3$ are independently selected from the group consisting of H, Na salt, K salt, Zn salt, Ca salt, Sn salt, and amine cation salt.

In another embodiment when ε is the site of attachment to a carbon atom in a polymer, $R_1$ has the structure of Formula 2. In a further embodiment when ε is the site of attachment to a carbon atom in a polymer, $R_1$ has the structure of Formula 2 and $R_4$ and $R_5$ are independently selected from the group consisting of H, Na salt, and K salt. In a further embodiment when ε is the site of attachment to a carbon atom in a polymer, $R_1$ has the structure of Formula 2 and $R_4$ and $R_5$ are independently selected from the group consisting of H, Na salt, K salt, Zn salt, Ca salt, Sn salt, and amine cation salt.

In another embodiment when ε is the site of attachment to a carbon atom in a polymer, $R_2$ has the structure of Formula 3. In another embodiment when ε is the site of attachment to a carbon atom in a polymer $R_2$ has the structure of Formula 3 and n is an integer from 1 to 3. In another embodiment when ε is the site of attachment to a carbon atom in a polymer, $R_2$ has the structure of Formula 3 and n is 1. In another embodiment when ε is the site of attachment to a carbon atom in a polymer, $R_2$ has the structure of Formula 3 and $R_6$ and $R_7$ are independently selected from the group consisting of H, Na salt, and K salt. In another embodiment when ε is the site of attachment to a carbon atom in a polymer, $R_2$ has the structure of Formula 3 and $R_6$ and $R_7$ are independently selected from the group consisting of H, Na salt, K salt, Zn salt, Ca salt, Sn salt, and amine cation salt. In another embodiment when ε is the site of attachment to a carbon atom in a polymer, $R_2$ has the structure of Formula 3, $R_6$ and $R_7$ are independently selected from the group consisting of H, Na salt, K salt, Zn salt, Ca salt, Sn salt, and amine cation salt, and n is 1.

In one embodiment when ε is the site of attachment to a carbon atom in a polymer, $R_8$ is H. In another embodiment, $R_8$ is $CH_3$.

In one embodiment when ε is the site of attachment to a carbon atom in a polymer, $L_1$ is a covalent bond. In another embodiment, $L_1$ has the structure of Formula 5. In another embodiment $L_1$ has the structure of Formula 5, the structure of X is selected from the group consisting of Formula 6, Formula 9 and Formula 11. In another embodiment, $L_1$ has the structure of Formula 5, X has the structure of Formula 6. In another embodiment, $L_1$ has the structure of Formula 5, X has the structure of Formula 7. In another embodiment, $L_1$ has the structure of Formula 5, X has the structure of Formula 9. In another embodiment, $L_1$ has the structure of Formula 5, X has the structure of Formula 11. In another embodiment, $L_1$ has the structure of Formula 5, X has the structure of Formula 6 and Y is alkanediyl. In another embodiment, $L_1$ has the structure of Formula 5, X has the structure of Formula 7 and Y is selected from the group consisting of alkanediyl and alkoxydiyl. In another embodiment, $L_1$ has the structure of Formula 5, X has the structure of of Formula 9 and Y is alkanediyl. In another embodiment, $L_1$ has the structure of Formula 5, X has the structure of Formula 11 and Y is alkanediyl.

In one embodiment when ε is the site of attachment to a carbon atom in a polymer, $R_{10}$, the chemical group resulting from polymer initiation, is selected from the structures of Formula 14-18:

Formula 14

Formula 15

Formula 16

Formula 17

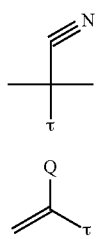

Formula 18 wherein:
R$_{12}$ is selected from the group consisting of —H, Na, K and amine cation salt;
τ is the site of attachment to polymer backbone and;
Q is the non-olefin residue of a monomer used in polymerization.

In one embodiment when ε is the site of attachment to a carbon atom in a polymer, M$_2$ is the polymerization residue of one or more co-monomers with the structure of Formula 19:

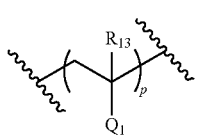

Formula 19 wherein:
R$_{13}$ is selected from the group consisting of —H or —CH$_3$;
Q$_1$ is the non-olefin residue of a co-monomer used in polymerization; and
p is an integer from 1 to 450.

Methods of Making Polymers and Composition

The site of attachment of the starting phosphonate structure can be on a polymer. The polymers of the present invention containing a phosphonate moiety can be made by a wide variety of techniques, including bulk, solution, emulsion, or suspension polymerization. Polymerization methods and techniques for polymerization are described generally in Encyclopedia of Polymer Science and Technology, Interscience Publishers (New York), Vol. 7, pp. 361-431 (1967), and Kirk-Othmer Encyclopedia of Chemical Technology, 3rd edition, Vol 18, pp. 740-744, John Wiley & Sons (New York), 1982, both incorporated by reference herein. See also Sorenson, W. P. and Campbell, T. W., Preparative Methods of Polymer Chemistry. 2nd edition, Interscience Publishers (New York), 1968, pp. 248-251, incorporated by reference herein, for general reaction techniques suitable for the present invention. In one example, the polymers are made by free radical copolymerization, using water soluble initiators. Suitable free radical initiators include, but are not limited to, thermal initiators, redox couples, and photochemical initiators. Redox and photochemical initiators may be used for polymerization processes initiated at temperatures below about 30° C. Such initiators are described generally in Kirk-Othmer Encyclopedia of Chemical Technology, 3rd edition, John Wiley & Sons (New York), Vol. 13, pp. 355-373 (1981), incorporated by reference herein. Typical water soluble initiators that can provide radicals at 30° C. or below include redox couples, such as potassium persulfate/silver nitrate, and ascorbic acid/hydrogen peroxide. In one example, the method utilizes thermal initiators in polymerization processes conducted above 40° C. Water soluble initiators that can provide radicals at 40° C. or higher can be used. These include, but are not limited to, hydrogen peroxide, ammonium persulfate, and 2,2'-azobis(2-amidinopropane) dihydrochloride. In one example, water soluble starting monomers are polymerized in a water at 60° C. using ammonium persulfate as the initiator.

The identity of chemical functional groups at the terminal ends of a linear polymer depend upon how the polymerization of that polymer chain was initiated and terminated. For free radical polymerization, any free radical in the system can begin a new chain. This free radical can be a direct derivative of the initiator such as a sulfate radical from persulfate, or alkyl radical from the azo type initiators (such as but not limited to 2,2'azobis(2-amidinopropane) dihydrochloride). The free radical can also be the result of a transfer reaction, for instance between a water and another radical to produce a hydroxyl radical or between a phosphate and another radical to produce a phosphate radical. Non-limiting examples of these resulting structures are given below, where R represents an H or appropriate counter ion such as Na, K or an amine and τ represents the site of attachment to the polymer.

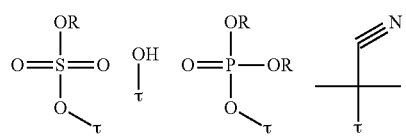

The free radical can also be the result of a chain transfer reaction, where the radical is transferred from a growing polymer chain to start a new chain. Chain transfer has been explicitly noted in polymerization of vinyl phosphonate monomers. Bingöl et al. Macromolecules 2008, 41, 1634-1639), incorporated by reference herein, describe how polymerization of alkyl esters of vinyl phosphonate result in chain transfer on the alkyl group. This transfer ultimately begins a new polymer chain with an olefin containing chemical group on the initiating end.

The chemical group on the terminating end of the polymer chain depends upon how the chain is terminated. The most common terminations are the previously mentioned chain transfer, backbiting followed by beta scission, combination and disproportionation. In chain transfer and backbiting, the terminating group is a hydrogen. In combination, the propagating radicals on two chains react to form a new chain. This reaction causes a "head to head" configuration at the point of attachment. The non-olefinic portions of the monomers that do not end up in the backbone of the chain are simply represented as Q.

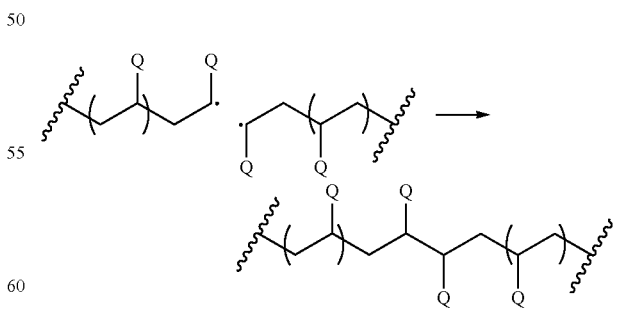

In disproportionation, a hydrogen is exchanged from one radical chain to another radical chain. The result is one chain is unsaturated while the other is saturated. Of note, the resulting unsaturated group is not a vinyl group. Each carbon in the unsaturation has only one hydrogen.

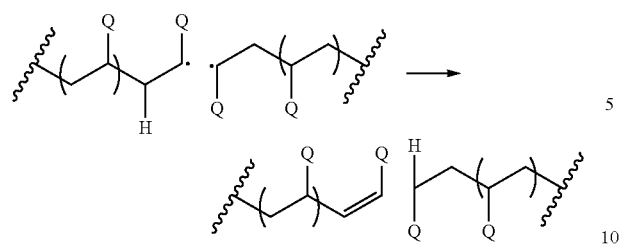

Numerous polymers containing phophonic acid or phosphonate groups are known with said phosphonic acid or phosphonate group directly off the backbone, in a side chain, or in a side group. The inventive methods described herein can be used to produce a phosphono-phosphate compound from said phosphonic acid or phosphonate groups. The following descriptions will exemplify different examples of suitable phosphonic acid or phosphonate containing polymers that can be reacted via this method.

As examples of polymers comprising a phosphonic acid or phosphonate group attached to a polymer backbone, consider the polymers made from the monomers vinyl phosphonate or methyl-vinyl phosphonate. Vinyl phosphonate or methyl-vinyl phosphonate can be chemically reacted by this method to form phosphono-phosphate monomers as shown in reaction 1 in Scheme 1 and described previously. Alternatively, vinyl phosphonate or methyl-vinyl phosphonate can be first polymerized as shown in reaction 3 to yield a polymer. After polymerization, the phosphono-phosphate group can be created by the methods described herein, thus creating a phosphono-phosphate group attached directly to the polymer backbone.

Scheme 1

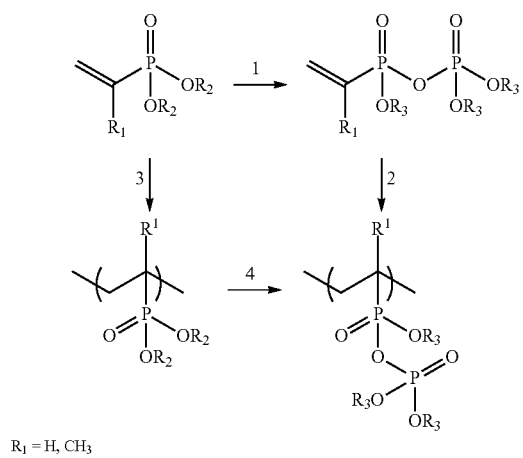

$R_1$ = H, $CH_3$
$R_2$ = H, Alkyl, Salts
$R_3$ = H, Salts, $P(O)(OR_3)_2$

A second example of a phosphonic acid or phosphonate group attached directly to the backbone can be exemplified by starting with polyethylene. For an example of the first reaction in such a modification, see M. Anbar, G. A. St. John and A. C Scott, J Dent Res Vol 53, No 4, pp 867-878, 1974. As shown in Scheme 2, polyethylene is first phosphorylated oxidatively with oxygen and $PCl_3$ to form a randomly phosphonated polymer. This phosphonated polymer can then be reacted via the described methods to produce a randomly substituted phosphono-phosphate polymer. The reaction products shown are meant to show the random nature of the points of attachment of the phosphonic acid or phosphonate groups in the polymer.

Scheme 2

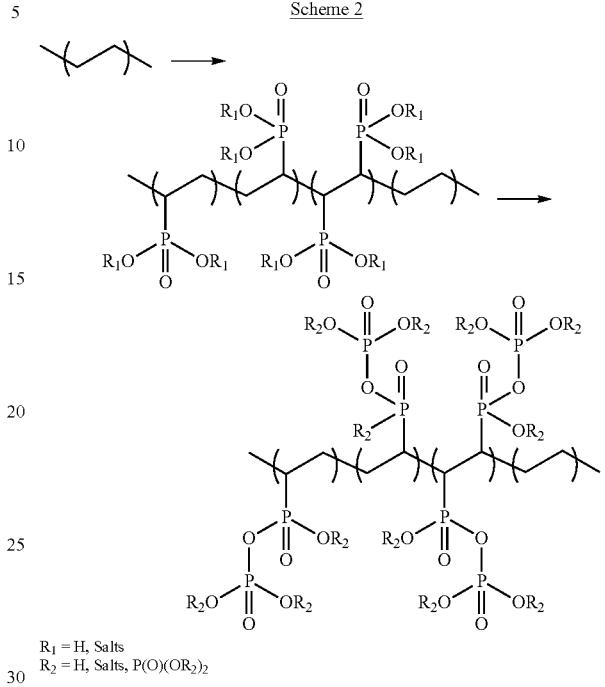

$R_1$ = H, Salts
$R_2$ = H, Salts, $P(O)(OR_2)_2$

As an example of the method with a phosphonic acid or phosphonate group attached to a side group, consider the vinyl benzyl chemistry depicted in Scheme 3. As with the previous example, this scheme will depict homopolymers for simplicity. However, heteropolymers having additional monomeric constituents could be made by including additional monomers in the polymerization process. 4-Vinylbenzyl chloride can be reacted with diethyl phosphite to form vinyl benzyl phosphonate depicted in reaction 1 of Scheme 3. For an example of this reaction, see Frantz, Richard; Durand, Jean-Olivier; Carre, Francis; Lanneau, Gerard F.; Le Bideau, Jean; Alonso, Bruno; Massiot, Dominique, Chemistry—A European Journal, Volume 9, Issue 3, pp. 770-775, 2003. Vinyl benzyl phosphonate can be reacted via this method to form vinyl benzyl phosphono-phosphate shown in reaction 2. Alternatively, the first intermediate, vinyl benzyl phosphonate, can be polymerized shown in reaction 4 to make poly vinyl benzyl phosphonate. For an example of this reaction, see M. Anbar, G. A. St. John and A. C Scott, J Dent Res Vol 53, No 4, pp 867-878, 1974. Poly vinyl benzyl phosphonate can then be reacted via the methods herein described, shown in reaction 7, to produce a phosphono-phosphate containing polymer where the phosphono-phosphate group is attached to a side group on the polymer. A second route involving a this method is also shown in the same scheme. 4-Vinylbenzyl chloride can be polymerized to provide poly vinyl benzyl chloride shown in reaction 3. This polymer can be phosphonated shown in reaction 6 (for example, see Sang Hun Kim, Young Chul Park, Gui Hyun Jung, and Chang Gi Cho, Macromolecular Research Vol 15 No 6 pp 587-597, 2007), and then the resulting poly vinly benzyl phosphonate reacted via the methods herein described to produce the phosphono-phosphate containing polymer shown as a product of reaction 7.

Scheme 3

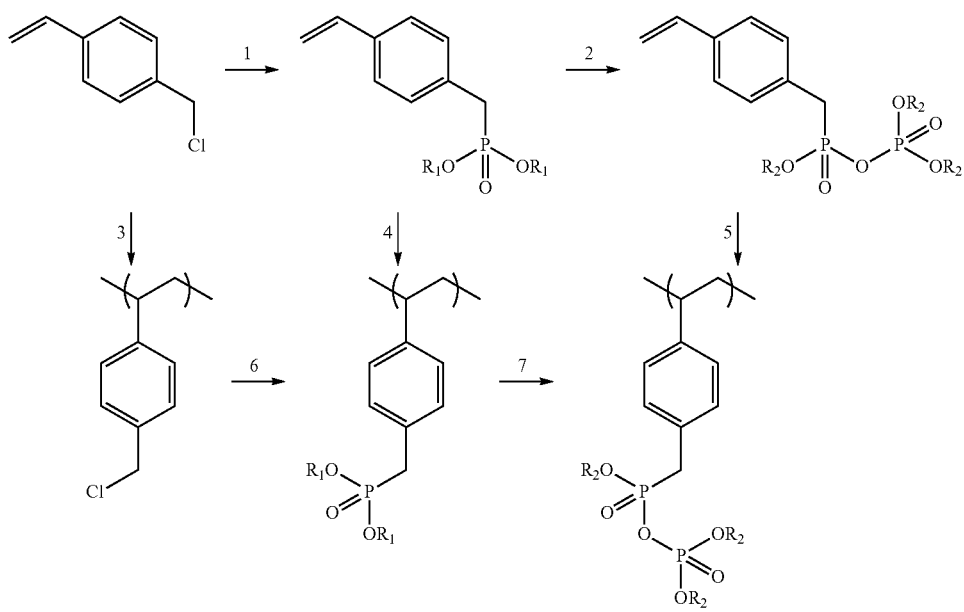

$R_1$ = H, Salts, Alkyl
$R_2$ = H, Salts, $P(O)(OR_2)_2$

As an example of polymers comprising a phosphonic acid or phosphonate group attached to a side chain and reacted via the methods described herein, consider the poly vinyl alcohol depicted in Scheme 4. The hydroxyl groups can be reacted with ethylene oxide to produce a polymer with PEG side chains. The terminating hydroxy on the side chains can be reacted with vinyl phosphonate, and then reacted via the methods described herein to form a phosphono-phosphate.

Scheme 4

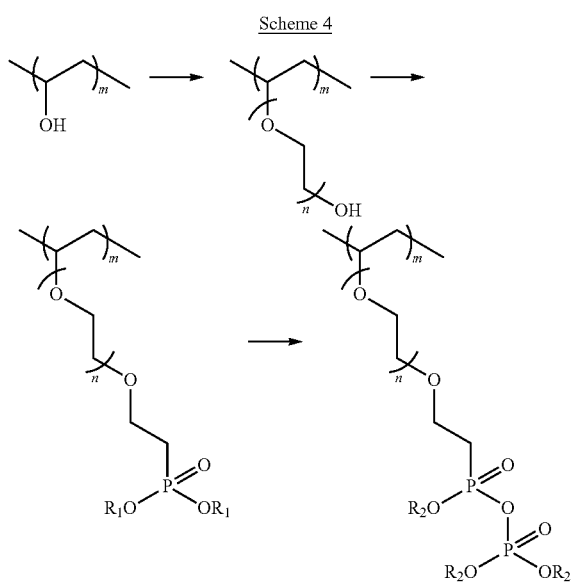

$m > n$
$R_1$ = H, Salts, Alkyl
$R_2$ = H, Salts, $P(O)(OR_2)_2$

The schemes depicted are not meant to be exhaustive in nature, but are meant to convey the various manners in which phosphono-phosphate containing polymers may be produced. The examples provide both technical details for synthesis and numerous variations of polymers containing phosphono-phosphate groups, both polymers with phosphono-phosphate groups attached directly to the polymer backbone and polymers with phosphono-phosphate groups attached to side groups. For further examples of phosphonate containing monomers and polymers that can be transformed into phosphono-phosphonate containing monomers and polymers, see Sophie Monge, Benjamin Canniccioni, Ghislain David and Jean-Jacques Robin, RSC Polymer Chemistry Series No. 11, Phosphorus-Based Polymers: From Synthesis to Applications, Edited by Sophie Monge and Ghislain David, The Royal Society of Chemistry 2014, Published by the Royal Society of Chemistry, www.rsc.org.

Uses of the Phosphono-Phosphate Containing Polymers

The phosphono-phosphate containing polymers according to the present invention can be incorporated into a variety of compositions. These compositions include both aqueous and non-aqueous compositions. The compositions are useful for treating teeth, hair, body, fabric, paper, nonwovens and hard surfaces. The compositions find utility in water treatments, boiler treatments, treating ship hulls, oil wells, batteries, baking, leavening, ceramics, plastics stabilizers, glass manufacture, cheese production, buffers in food, abrasives in dentifrice, binders in meat, coffee creamers, antifreeze, dispersing agents in paints liquid soaps, metal cleaners synthetic rubber, textiles and flame retardants. The compositions are also useful for treating materials containing multivalent metal cations including but not limited to calcium, tin, magnesium and iron. Examples of such materials include hydroxyapatite, calcium carbonate (amorphous, calcite, aragonite), calcium phosphate, calcium hydroxide, magnesium carbonate, magnesium phosphate, soap scum (mixture of calcium, magnesium, and iron salts of stearic acid and carbonate), and hard water stains. In one embodiment, the composition comprising phosphono-phosphate containing polymers is non-aqueous. In another embodiment, the composition is aqueous.

The phosphono-phosphate containing compounds and polymers can be applied to a variety of substrates. Embodiments of substrates include biological material, fabric, non-woven materials, paper products and hard surface materials. In one embodiment, the biological material comprises teeth. In another embodiment, the biological material comprises keratin, such as hair or skin.

EXAMPLES

The following examples further describe and demonstrate the preferred embodiments within the scope of the present invention. The examples are given solely for the purpose of illustration and are not to be construed as limitations of the present invention since many variations thereof are possible without departing from the spirit and scope of the invention. Ingredients are identified by chemical name, or otherwise defined below.

General Chemical Scheme for Examples 1-6:
Synthesis of Vinyl Phosphono-monoPhosphate (VPP) or [Vinylphosphonic Phosphoric Anhydride] and Other Extended Vinyl Phosphono-Phosphates (eVPP) by Removal of Water The following chemical scheme shows general reaction scheme in examples 1-5 used to form the primary desired products, VPP and VPPP, along with some of the other products observed in some but not all of the following experiments. Please refer to individual examples for final identified product distributions.

1 mL D7-DMF with 0.25 mL tributyl amine, and evaluated by P-NMR. The final product was found to contain VPA, Vinyl-Phosphono-monoPhosphate (VPP), Vinyl-Phosphono-Pyrophosphate (VPPP), Vinyl-Phosphonic Acid Anhydride (VPPV), Phosphoric acid (PA), Pyrophosphoric Acid (PP) & Tri-Phosphoric Acid (PPP). Species identification was confirmed using LCMS. In addition H-NMR was run on the final 27 hour sample from which it was determined that no polymerization occurred during the reaction.

Final molar distributions of all vinyl containing species in the melt at 27 hours was found to be 43% VPA, 38% VPP, 9% VPPP, and 10% VPPV.

Example 2—Synthesis of VPP and eVPP by Evaporation Using Vacuum and a Sweep Gas with 3 Equivalents of PA The procedure of example 1 was followed with the following changes. The short path distillation head was connected to a Buchi vacuum pump rather than venting to atmosphere. The round bottom flask was evacuated to 50-60 Torr for the duration of the experiment with constant flow of nitrogen from one side neck. Sampling at 32 and 48 hours showed little change between the time points with a vinyl containing distribution of 31-32% VPA, 40-41% VPP, 14% VPPP, and 13-14% VPPV. Signals corresponding to VPPPV were also observed in P-NMR but were not quantified do to overlap with other peaks.

Example 3—Synthesis of VPP and eVPP by Evaporation Using Vacuum and a Sweep Gas with 6 Equivalents of PA The procedure of example 2 was followed with 6 equivalents of PA relative to VPA. The distribution of vinyl

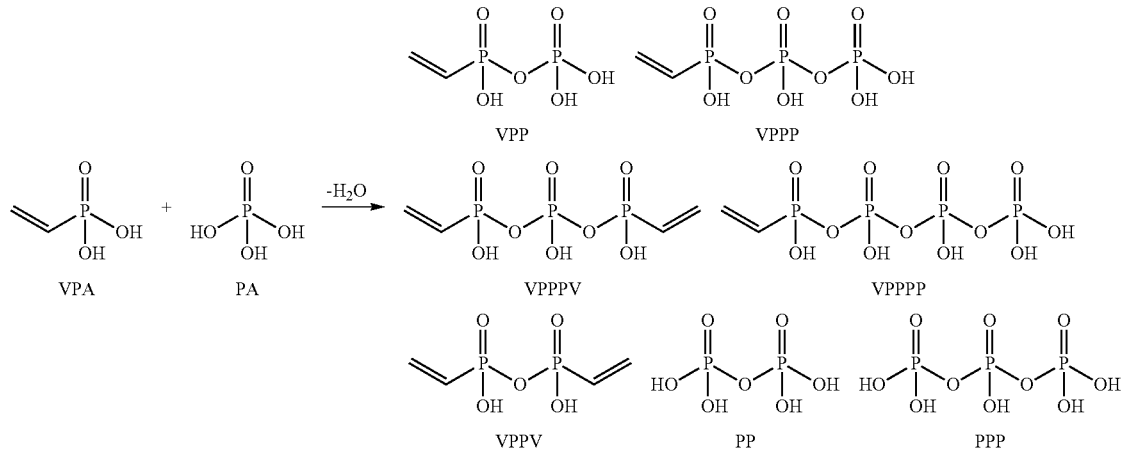

Example 1—Synthesis of VPP and eVPP by Evaporation Using a Sweep Gas with 3 Equivalents of PA A 50 mL 3 neck round bottom flask, equipped with a magnetic stirrer and a short path distillation head in the middle neck, was charged with 1 gram of vinyl phosphonic acid (VPA) and 2.72 g (3 equivalents) of 99% phosphoric acid (PA). One side neck was stoppered, and nitrogen was swept through the other side neck and out through the distillation head. The flask was placed in oil bath heated to 105° C. and stirred at that temperature for 27 hours. Samples (~1 drop) were removed at desired time points, dissolved in containing species at 72 hours was 31% VPA, 40% VPP, 21% VPPP, and 8% VPPV. Signals corresponding to VPPPV were also observed in P-NMR but were not quantified do to overlap with other peaks.

Example 4—Synthesis of VPP and eVPP by Reaction with Phosphorous Anhydride ($P_2O_5$, Phosphorous Pentoxide)

To a magnetically stirred 20 mL scintillation vial was added 2.24 g of 85 weight % phosphoric acid in water, 1.01 g 90% vinyl phosponic acid and 2.5 phosphorous pentoxide (in that order). The molar ratio of vinyl phosphonate to total phosphate (calculated as the sum of the moles of phosphate plus twice the moles of P$_2$O) as 6. The vial was heated to 175° C. and sampled for P NMR at 1 hour using the procedure of example 1. The molar composition of identified vinyl containing species was 34% VPA, 41% VPP, 19% VPPP and 5% VPPV. Additional vinyl peaks were visible in P NMR that likely correspond to larger species including VPPPP, and VPPPPP. LCMS confirmed the existence of higher order phosphono-phosphates with peaks for VPP, VPPP, VPPPP, VPPPPP, VPPPPPP, and VPPPPPPP all visible in negative ion mode.

Example 5—Scale Up and Purification of Example 2

The procedure of Example 2 was followed with a 5-fold increase in total materials. Sampling at 32 hours showed a distribution of vinyl containing species of 35% VPA, 37% VPP, 12% VPPP, 12% VPPV and 4% VPPPV.

After cooling, the bulk of the crude reaction mixture was dissolved in 40 ml anhydrous DMF. The dissolved solution was added to a solution of 28.1 g triethyl amine (1.5 equivalents based on total starting acid) in 100 mL of anhydrous DMF with rapid stirring over 5 min. The P-NMR was run on the resultant solution and was consistent with distributions from the crude reaction mixture.

The resultant solution was stripped of DMF at 70° C. & 25 Torr yielding 38.4 g viscous yellow oil. This was dissolved in 100 mL H$_2$O yielding a solution with a pH of 2.5, which was adjusted to 11.0 with 110 g 10% NaOH yielding a clear solution. The P-NMR was run on the resultant solution which showed a consistent product distribution as previous samples, but with an approximate 20% reduction in VPPV. Upon standing at room temperature for 1 hour, a white precipitant formed which was collected by filtration, dried overnight in ambient air to 4.65 g This precipitant was found to be about 90% pyrophosphate, with 4% phosphate and less than 3% each of VPA, VPP and PPP. The filtrate was stripped of solvent yielding 49.4 g clear viscous oil. The pH of the resultant oil was checked by litmus and found to be around 7. This was brought up to approximately 125 g with additional water yielding a pH of 7.5 which was adjusted to 11.0 with 15.2 g 1N NaOH. To this pH 11 solution was added 250 ml MeOH with rapid stirring over 30 min. at room temperature. A white precipitant formed over the course of one hour. This precipitant was collected by filtration, rinsed one time with 50 mL 2:3 H$_2$O:MeOH and dried under ambient air overnight to 17.9 g. This precipitant was found to be approximately 43% pyrophosphate, 39% phosphoric acid, 10% PPP, 3% VPP and 4% VPPP. The MeOH water solution was concentrated under flowing nitrogen overnight at room temperature to yield 31.1 g of viscous oil. The oil was found to have a molar phosphorous distribution of approximately 33% VPA, 33% VPP, 8% VPPP, 11% PA, 10% VPPV and 3% VPPPV. The oil was also found to have residual water and DMF.

To the oil, 300 ml MeOH was added over 1 hr at room temperature yielding a white precipitant which was collected by filtration, rinsed 1×50 mL MeOH and dried under vacuum at room temperature for 2 hrs to yield 4.3 g white powder. The powder was found to have a molar phosphorous distribution of 49% VPP, 26% PA, 6% PP, 15% VPPP and 3% VPA. The MeOH solution was concentrated under flowing nitrogen at room temperature 7.0 g white paste. The composition of the white paste was found to be approximately 73% VPA, 23% VPP and 5% VPPPV.

Example 6—Polymerization to Create VPPP Containing Polymer

The white powder from example 5 containing 49% VPP, 26% PA, 6% PP, 15% VPPP and 3% VPA, was polymerized using a 50/50 mixture (total molar vinyl basis) of the white VPPP containing powder (8.6 mmol vinyl groups) and SVS (8.6 mmol vinyl groups). Specifically, the white VPPP containing powder (Example 5, 8.6 mmoles) and SVS (25% aqueous solution, 4.47 g, 8.6 mmoles), were charged in a round bottom flask, and the headspace of the flask purged with flowing nitrogen for 15 minutes. The flask was sealed and heated to 60° C. at which time Ammonium Persulfate (APS, Aldrich, 5% relative to total monomers) was added in 0.50 ml water. The resultant was stirred 24 hrs at 60° C.

The crude reaction solutions were diluted to 1 wt % polymer in water and the pH adjusted to 8.5. These solutions were dialyzed with 2K molecular weight cut off dialysis membranes against reverse osmosis water for 5-7 days.

Water was removed from the product by freeze drying yielding 3.6 white solid.

The phosphonate content in the polymers were determined by preparing an NMR sample with purified polymer & trimethyl phosphate (TMP) in D$_2$O. The $^1$H & $^{31}$P-NMR's were run from which the phosphonate content was calculated from the H and P peaks of the internal standard relative (TMP) relative to the polymer peaks and water. The P-NMR shows broad phosphono-phosponate peaks at ~18 to 23 ppm and −6 to −10 ppm in approximately 1:1 ratio and also a phosphonate peak at ~26-28 ppm. The polymer was found to contain 57% monomers based on SVS, and 43% based on phosphonates. The phosphonate distribution was 3% from VPA, 78% from VPP and 18% from VPPP. The polymer was 78% active on a weight basis with 22% impurities/water.

Example 7—Synthesis of VPP and eVPP by Reaction with Phosphoric Acid and Urea

For all samples in the example, the following general procedure was followed:

A scintillation vial was charged with VPA, 85% or 99% H$_3$PO$_4$, urea & water as noted in the Table 1 below. The resultant was stirred at 60° C. for approximately 15 minutes until a homogenous solution was obtained. The resultant solution was transferred hot into an 800 mL beaker. This was placed in a programmable lab oven with circulating air flow and exterior ventilation. All samples were heated as follows:
1) Ramped from room temperature to 110° C. over 15 minutes.
2) Hold at 110° C. 3 hours.
3) Ramped from 110° C. to 150° C. over 15 minutes.
4) Hold at 150° C. for either 15 or 60 minutes as noted in table below.
5) Cooled to room temperature and allow to stand overnight.

P-NMR was run on the crude reaction products (~50 mg reaction product in 1 mL D$_2$O with 5 drops 30% NaOD). The products were found to contain VPA, vinyl-phosphono-phosphate (VPPA), vinyl-phosphono-pyrophosphate (VP-PPA), vinylphosphonic anhydride (SM-An), phosphoric acid (PA), pyrophosphoric acid & tri-phosphoric acid (PPP). Areas from P-NMR are shown in Table 1 below. H-NMR's were also run on the reaction products to check for polymerization of the VPA during the heating. No polymer was observed.

| Rx # | % Areas from P NMR ||||| Sample Prep & Rx Conditions |||||||
|---|---|---|---|---|---|---|---|---|---|---|---|---|---|
| | VPA | VPPA | VPPPA | SM-An | VPPA + VPPPA | g VPA | g H2O | g H3PO4/% | g Urea | Equiv VPA | Equiv H3PO4 | Equiv Urea | Time 150° C. |
| 1 | 46.9 | 22.7 | 5.0 | 25.4 | 27.7 | 0.5 | 1.5 | 0.58 g 85% | 0.33 | 1 | 1.1 | 1.2 | 15 min |
| 1 | 48.9 | 29.5 | 7.1 | 14.4 | 36.6 | 0.5 | 1.5 | 1.16 g 85% | 0.66 | 1 | 2.2 | 2.4 | 15 min |
| 3 | 33.4 | 38.5 | 13.4 | 14.8 | 51.8 | 0.5 | 1.5 | 1.75 g 85% | 1 | 1 | 3.3 | 3.6 | 15 min |
| 4 | 36.4 | 40.2 | 15.7 | 7.6 | 56.0 | 0.5 | 1.5 | 3.48 g 85% | 2 | 1 | 6.6 | 7.2 | 15 min |
| 5 | 100.0 | 0.0 | 0.0 | 0.0 | 0.0 | 0.5 | 1.5 | 3.48 g 85% | 0 | 1 | 6.6 | 0 | 15 min |
| 6 | 33.1 | 38.1 | 19.2 | 9.6 | 57.3 | 0.5 | 0 | 2.95 g 99% | 2 | 1 | 6.6 | 7.2 | 15 min |
| 7 | 48.5 | 34.3 | 10.5 | 6.7 | 44.8 | 0.5 | 1.5 | 3.48 g 85% | 2 | 1 | 6.6 | 7.2 | 60 min |
| 8 | 45.8 | 36.2 | 11.1 | 6.9 | 47.3 | 0.5 | 0 | 3.48 g 85% | 2 | 1 | 6.6 | 7.2 | 60 min |
| 9 | 54.7 | 29.5 | 7.4 | 8.4 | 36.9 | 0.5 | 0 | 1.75 g 85% | 1 | 1 | 3.3 | 3.6 | 60 min |
| 10 | 54.1 | 32.1 | 8.3 | 5.5 | 40.4 | 0.5 | 0 | 2.95 g 99% | 2 | 1 | 6.6 | 7.2 | 60 min |
| 11 | 32.1 | 38.1 | 21.9 | 7.8 | 60.1 | 0.5 | 0 | 3.48 g 85% | 2 | 1 | 6.6 | 7.2 | 15 min |
| 12 | 41.7 | 32.4 | 14.0 | 11.9 | 46.4 | 0.5 | 0 | 1.75 g 85% | 1 | 1 | 3.3 | 3.6 | 15 min |
| 13 | 33.0 | 36.5 | 22.0 | 8.5 | 58.5 | 0.5 | 0 | 2.95 g 99% | 2 | 1 | 6.6 | 7.2 | 15 min |
| 14 | 40.2 | 29.6 | 17.0 | 13.2 | 46.6 | 0.5 | 0 | 3.48 g 85% | 4 | 1 | 6.6 | 14.4 | 15 min |
| 15 | 42.7 | 25.7 | 22.7 | 8.9 | 48.4 | 0.5 | 0 | 1.75 g 85% | 2 | 1 | 3.3 | 7.2 | 15 min |

Example 8—Synthesis of Polymer Containing VPP and eVPP by Reaction of Polymer with Phosphoric Acid and Urea

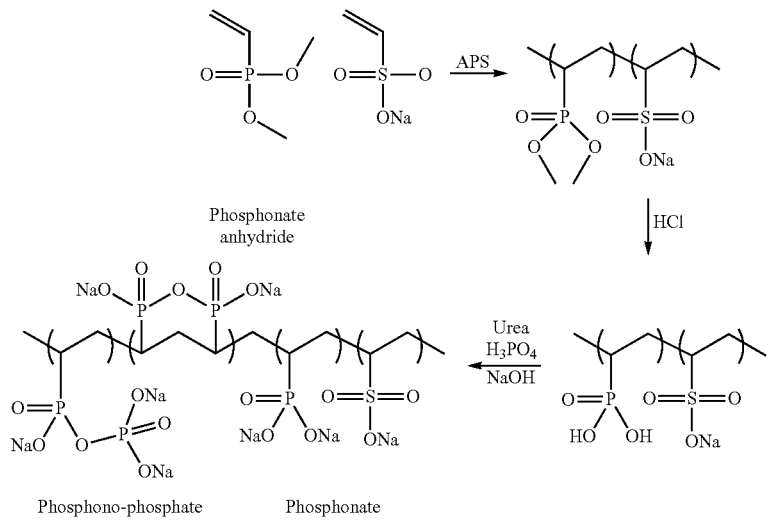

Dimethyl vinyl phosphonate, DMVP (10.6 g, 77.9 mmoles) and sodium vinyl sulfonate solution, SVS (25% aqueous solution, 40.5 g, 77.9 mmoles), were charged in a 100 mL round bottom flask. The flask was purged with nitrogen for 15 minutes and heated to 60° C. Ammonium persulfate APS, 888 mg, 2.55% of total monomer, was brought up in 4 g of water and degassed with nitrogen for 5 minutes. The APS solution was added to the solution containing DMVP and SVS and resultant solution was allowed to stir for 24 hours under nitrogen at 60° C.

$^1$H-NMR & $^{31}$P-NMR were run on the crude reaction solution, and a monomer conversion of around 99% was observed with a broad P polymer peak at −37 ppm from the phosphonate group.

The crude reaction solution was diluted to 10 wt % polymer in water with 207 g of water. To this was added 300 mL of acetone over 30 minutes under continuous stirring at room temperature to yield a turbid solution. After standing in a separatory funnel for 30 minutes a lower viscous polymer rich syrup and upper fluid organic layer were formed. The lower layer was collected, solvent evaporated under nitrogen overnight followed by vacuum, 2 hours at 1 Torr to yield 15.3 grams of a tacky tan solid. $^1$H-NMR & $^{31}$P-NMR were run on this solid with an internal standard, trimethyl phosphate, to show a 50:50 ratio of DMVP:SVS derived groups.

The tacky tan solid was mixed with 30 grams of water and 45 grams of concentrated HCl (≈37%) to yield a milky white solution. This mixture was refluxed for 48 hours to yield a transparent solution with a slight brown color. The water and HCl were stripped from the solution on a roto-vap operating at 60° C. and 20 torr to a total volume of ≈20 mL. 100 additional mL of water was added to this remaining fraction and the stripping was repeated, then 200 mL of water was added, the sample was frozen and lyophilized to yield 11.8 g of tan solid. $^{31}$P-NMR showed a shift in the polymer beak from ≈37 to ≈32 ppm, while the $^1$H-NMR showed the disappearance of the peak polymer peak at ≈3.8 ppm that corresponded to the methyl ester peak. Analysis with an internal standard indicated a ratio of P containing groups to sulfur containing groups of approximately 47 to 53, and a weight activity of 82.4%.

A 100 mL beaker was charged with 4.85 grams of 85% phosphoric acid and 2.77 grams of urea and heated to 60° C.

for 15 minutes then cooled to room temperature to yield a clear solution. 5 grams of 82.4% active polymer with a calculated ratio of P to S of 47 to 53 was dissolved in 15 mL of water and this was added to the phosphoric acid/urea mixture in the 100 mL beaker. This was placed in a programmable lab oven with circulating air flow and exterior ventilation and heated as follows:

1) Ramped from room temperature to 110° C. over 15 minutes.
2) Hold at 110° C. 3 hours.
3) Ramped from 110° C. to 150° C. over 15 minutes.
4) Hold at 150° C. for 15 minutes.
5) Cooled to room temperature and allow to stand overnight.

11.4 grams of spongy white product was collected. P-NMR was run on the crude reaction products (~150 mg reaction product in 1 mL $D_2O$ with 2 drops 30% NaOD). P-NMR demonstrated a broad peak at ≈−5 ppm corresponding to a phosphono-phosphate group on a polymer chain. A portion of this peak is overlapped by pyrophosphate making quantification difficult.

The bulk of the crude, 11.4 g, was dissolved in 50 mL of water, charged to a round bottom flask under stirring and 50 mL of methanol added over 30 minutes to yield a turbid solution. Upon standing in a separatory funnel for 30 minutes, a lower viscous polymer rich syrup layer resulted which was separated (9.5 g). The ratio of polymer to phosphate to pyrophosphate was evaluated by P-NMR and found to be 161 to 43 to 113.

The precipitation was repeated on the above 9.5 grams of syrup using 50 mL of water and 50 mL of methanol. 2.13 g syrup resulted. P-NMR showed the polymer to phosphate to pyro ratio to be 158 to 3 to 18.

The resultant syrup was brought up to 250 mL of reverse osmosis (RO) water further purified by dialysis in a Thermo Scientific Slide-A-Lyzer dialysis flask (2K MWCO) against RO water (pH adjusted to 8.5 w sat sodium bicarbonate solution) for 6 days. The water was removed by freezing and lyophilization yielding 1.59 grams white solid. $^1$H-NMR & $^{31}$P-NMR showed the collected polymer to be ≈41% P monomers, and 59% S monomers. Analysis of the P containing groups showed ≈22% phosphono-phosphate groups with a small amount of phosphono-pyrophosphate groups. The remaining P containing groups appeared to be a mixture of phosphonate and phosphonate anhydride structures. The polymer was calculated as 87.4% weight active.

It is understood that the examples and embodiments described herein are for illustrative purposes only and that various modifications or changes in light thereof will be suggested to one skilled in the art without departing from its spirit and scope.

What is claimed is:

1. A method of making a phosphono-phosphate compound comprising the steps of:
   a. mixing a first component comprising a phosphonic acid, a phosphonate or mixtures thereof, with a second component comprising a source of phosphoric acid or phosphate, wherein the mixture has a molar phosphorous ratio of said first component to said second component of from 1:1 to 1:10, and
   b. physically dehydrating the mixture to produce a phosphono-phosphate compound having the structure of Formula 1:

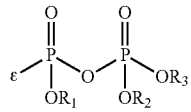

Formula 1 wherein:
ε is the site of attachment to a carbon atom;
$R_1$ is selected from the group consisting of —H, metal salt having Na, K, Ca, Mg, Mn, Zn, Fe, or Sn cation, amine cation salt, and a structure of Formula 2:

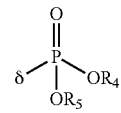

Formula 2 wherein:
δ is the site of attachment to Formula 1,
$R_4$ and $R_5$ are independently selected from the group consisting of —H, metal salt having Na, K, Ca, Mg, Mn, Zn, Fe, or Sn cation, and amine cation salt;
$R_2$ is selected from the group consisting of —H, metal salt having Na, K, Ca, Mg, Mn, Zn, Fe, or Sn cation, amine cation salt, and a structure of Formula 3:

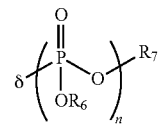

Formula 3 wherein:
δ is the site of attachment to Formula 1,
$R_6$, and $R_7$ are independently selected from the group consisting of —H, metal salt having Na, K, Ca, Mg, Mn, Zn, Fe, or Sn cation, and amine cation salt, and
n is an integer from 1 to 2 and;
$R_3$ is selected from the group consisting of —H, metal salt having Na, K, Ca, Mg, Mn, Zn, Fe, or Sn cation, and amine cation salt.

2. The method of claim 1 wherein said physical dehydration is accomplished by the evaporation of water.

3. The method of claim 2 wherein said evaporation of water is performed at a temperature greater than 100° C.

4. The method of claim 2 wherein said evaporation of water is performed at a pressure lower than atmospheric pressure.

5. The method of claim 2 wherein said evaporation of water is performed with the aid of a sweep gas.

6. The method of claim 2 wherein said evaporation of water is performed at a temperature greater than 100° C. and at a pressure lower than atmospheric.

7. The method of claim 2 wherein said evaporation of water is performed at a temperature greater than 100° C., at a pressure lower than atmospheric, and with the aid of a sweep gas.

8. The method of claim 1 wherein said source of phosphoric acid or phosphate is selected from the group consisting of phosphoric acid, dihydrogen phosphate, monohydrogen phosphate, phosphate, pyrophosphoric acid, trihydrogen pyrophosphate, dihydrogen pyrophosphate, monohydrogen pyrophosphate, pyrophosphate, triphosphoric acid, tetrahydrogen triphosphate, trihydrogen triphosphate, dihydrogen triphosphate, monohydrogen triphosphate, triphosphate, mixtures of phosphorous pentoxide and water, and mixtures thereof.

9. The method of claim 1 wherein said source of phosphoric acid or phosphate is phosphoric acid.

10. The method of claim 1 wherein said source of phosphoric acid or phosphate is a mixture of phosphorous pentoxide and water.

11. The method of claim 1 wherein said source of phosphoric acid or phosphate is phosphoric acid, phosphorous pentoxide, and water.

12. A method of making a phosphono-phosphate compound comprising the steps of:
c. mixing a first component comprising a phosphonic acid, a phosphonate or mixtures thereof, with a second component comprising a source of phosphoric acid or phosphate, wherein the mixture has a molar phosphorous ratio of said first component to said second component of from 1:1 to 1:10, and
d. chemically dehydrating the mixture to produce a phosphono-phosphate compound with the structure of Formula 1:

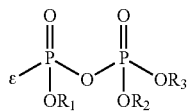

Formula 1 wherein:
ε is the site of attachment to a carbon atom;
$R_1$ is selected from the group consisting of —H, metal salt having Na, K, Ca, Mg, Mn, Zn, Fe, or Sn cation, amine cation salt, and a structure of Formula 2:

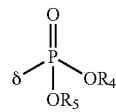

Formula 2 wherein:
δ is the site of attachment to Formula 1,
$R_4$ and $R_5$ are independently selected from the group consisting of —H, metal salt having Na, K, Ca, Mg, Mn, Zn, Fe, or Sn cation, and amine cation salt;
$R_2$ is selected from the group consisting of —H, metal salt having Na, K, Ca, Mg, Mn, Zn, Fe, or Sn cation, amine cation salt, and a structure of Formula 3:

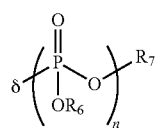

Formula 3 wherein:
δ is the site of attachment to Formula 1,
$R_6$, and $R_7$ are independently selected from the group consisting of —H, metal salt having Na, K, Ca, Mg, Mn, Zn, Fe, or Sn cation, and amine cation salt, and
n is an integer from 1 to 2 and;
$R_3$ is selected from the group consisting of —H, metal salt having Na, K, Ca, Mg, Mn, Zn, Fe, or Sn cation, and amine cation salt.

13. The method of claim 12 wherein said chemical dehydrating is accomplished by a chemical reaction with a chemical dehydration agent.

14. The method of claim 13 wherein said chemical dehydration agent is phosphorous pentoxide.

15. The method of claim 12 wherein said source of phosphoric acid or phosphate is selected from the group consisting of phosphoric acid, dihydrogen phosphate, monohydrogen phosphate, phosphate, pyrophosphoric acid, trihydrogen pyrophosphate, dihydrogen pyrophosphate, monohydrogen pyrophosphate, pyrophosphate, triphosphoric acid, tetrahydrogen triphosphate, trihydrogen triphosphate, dihydrogen triphosphate, monohydrogen triphosphate, triphosphate, mixtures of phosphorous pentoxide and water, and mixtures thereof.

16. The method of claim 12 wherein said source of phosphoric acid or phosphate is phosphoric acid.

17. The method of claim 12 wherein said source of phosphoric acid or phosphate is a mixture of phosphorous pentoxide and water.

18. The method of claim 12 wherein said source of phosphoric acid or phosphate is phosphoric acid, phosphorous pentoxide, and water.

19. The method of claim 12 wherein said source of phosphoric acid or phosphate is a mixture of phosphorous pentoxide and water, and said chemical dehydrating is accomplished by use of a chemical dehydration agent wherein said chemical dehydration agent is phosphorous pentoxide.

20. The method of claim 12 wherein said source of phosphoric acid or phosphate is phosphoric acid, phosphorous pentoxide and water, and said chemical dehydrating is accomplished by use of a chemical dehydration agent wherein said chemical dehydration agent is phosphorous pentoxide.

21. The method of claim 1, further comprising the step of:
c) neutralizing the dehydrated mixture with a basic salt comprising Na, K, Ca, Mg, Mn, Zn, Fe, Sn, or amine cations.

22. The method of claim 12, further comprising the step of: c) neutralizing the dehydrated mixture with a basic salt containing Na, K, Ca, Mg, Mn, Zn, Fe, Sn, or amine cations.

23. The method of claim 1, further comprising the step of: c) neutralizing the dehydrated mixture with an amine cation, and further reacting the resulting mixture with a basic salt comprising Na, K, Ca, Mg, Mn, Zn, Fe or Sn to form a metal phosphono-phosphate salt.

24. The method of claim 12, further comprising the step of: c) neutralizing the dehydrated mixture with an amine cation, and further reacting the resulting mixture with a basic salt comprising Na, K, Ca, Mg, Mn, Zn, Fe or Sn to form a metal phosphono-phosphate salt.

25. The method of claim 23, further comprising the step of: d) precipitating said metal phosphono-phosphate salt from solution.

26. The method of claim 24, further comprising the step of: d) precipitating said metal phosphono-phosphate salt from solution.

* * * * *